(12) United States Patent
Squitieri et al.

(10) Patent No.: US 11,981,099 B2
(45) Date of Patent: *May 14, 2024

(54) METHODS FOR CONTROLLING AND MONITORING INFLATABLE PERFUSION ENHANCEMENT APPARATUSES AND ASSOCIATED SYSTEMS

(71) Applicant: TurnCare, Inc., Palo Alto, CA (US)

(72) Inventors: Rafael Paolo Squitieri, Wilton, CT (US); Robert Charles Deutsch, Oakridge, CA (US); Steven Bruce Frazier, Sloatsburg, NY (US); Robert Loiacono, Young Harris, GA (US); Linda Seaman, Bridgeport, CT (US); Erica Kelly, Bridgeport, CT (US)

(73) Assignee: TurnCare, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/583,944

(22) Filed: Jan. 25, 2022

(65) Prior Publication Data

US 2022/0142840 A1    May 12, 2022

Related U.S. Application Data

(60) Division of application No. 16/584,704, filed on Sep. 26, 2019, now Pat. No. 11,504,927, which is a
(Continued)

(51) Int. Cl.
*B29D 22/02* (2006.01)
*A61F 5/32* (2006.01)
(Continued)

(52) U.S. Cl.
CPC ............. *B29D 22/02* (2013.01); *A61F 5/32* (2013.01); *A61F 5/34* (2013.01); *A61G 7/05776* (2013.01);
(Continued)

(58) Field of Classification Search
CPC .. A61F 5/05816; A61F 5/34; A61F 13/51474; A47C 27/083; A61H 9/0078; F16K 31/004; A61G 7/0527
See application file for complete search history.

(56) References Cited

U.S. PATENT DOCUMENTS

| 4,175,297 A | 11/1979 | Richardson et al. |
| 4,967,756 A | 11/1990 | Hewitt |

(Continued)

FOREIGN PATENT DOCUMENTS

| EP | 2250988 A2 | 11/2010 |
| JP | H01202433 A | 8/1989 |

(Continued)

*Primary Examiner* — Dah-Wei D. Yuan
*Assistant Examiner* — Andrew J Bowman
(74) *Attorney, Agent, or Firm* — Perkins Coie LLP; Andrew T. Pettit

(57) ABSTRACT

Introduced here are methods, apparatuses, and systems for mitigating the contact pressure applied to a human body by the surface of an object, such as a chair, bed, or table. A pressure-mitigation apparatus can include a series of chambers whose pressure can be individually varied. When placed between a patient and a contact surface, a controller can vary the contact pressure on the human body by controllably inflating one or more chambers, deflating one or more chambers, or any combination thereof. By monitoring the pressure in each chamber over time, the controller can also gain an enhanced understanding of movement(s) performed by the human body when positioned on the pressure-mitigation apparatus.

19 Claims, 17 Drawing Sheets

Related U.S. Application Data continuation-in-part of application No. 16/363,094, filed on Mar. 25, 2019.

(60) Provisional application No. 62/736,758, filed on Sep. 26, 2018, provisional application No. 62/690,206, filed on Jun. 26, 2018, provisional application No. 62/647,551, filed on Mar. 23, 2018.

(51) Int. Cl.
    *A61F 5/34*         (2006.01)
    *A61G 7/057*      (2006.01)
    *A61L 31/10*      (2006.01)
    *A61L 31/14*      (2006.01)

(52) U.S. Cl.
    CPC .............. *A61L 31/10* (2013.01); *A61L 31/14* (2013.01); *A61G 2203/34* (2013.01); *A61L 2420/02* (2013.01)

(56) References Cited

U.S. PATENT DOCUMENTS

| | | | |
|---|---|---|---|
| 5,461,741 A | 10/1995 | Graebe | |
| 5,840,050 A | 11/1998 | Lerman | |
| 6,237,598 B1 | 5/2001 | Sereboff | |
| 6,901,617 B2 | 6/2005 | Sprouse et al. | |
| 7,188,620 B2 | 3/2007 | Amarasinghe | |
| 9,901,491 B2 | 2/2018 | Squitieri | |
| 2002/0104165 A1 | 8/2002 | Gross | |
| 2004/0034936 A1* | 2/2004 | Welling | A61G 7/0527 5/624 |
| 2004/0048062 A1 | 3/2004 | Nonaka et al. | |
| 2004/0206409 A1* | 10/2004 | Yano | F16K 31/004 137/883 |
| 2006/0149176 A1* | 7/2006 | Bolam | A61H 9/0078 601/150 |
| 2007/0118993 A1 | 5/2007 | Bates | |
| 2008/0201853 A1 | 8/2008 | Graebe | |
| 2010/0042026 A1 | 2/2010 | Kloecker et al. | |
| 2011/0185508 A1 | 8/2011 | Hsu et al. | |
| 2012/0304384 A1 | 12/2012 | Scholz et al. | |
| 2013/0219626 A1 | 8/2013 | Clapper | |
| 2013/0255699 A1* | 10/2013 | Squitieri | A61F 13/51474 128/892 |
| 2014/0059781 A1* | 3/2014 | Lafleche | A47C 27/083 5/713 |
| 2015/0224005 A1 | 8/2015 | Kramer et al. | |
| 2015/0238378 A1 | 8/2015 | Bhat et al. | |
| 2016/0193090 A1 | 7/2016 | Squitieri et al. | |
| 2019/0021918 A1 | 1/2019 | Squitieri | |

FOREIGN PATENT DOCUMENTS

| | | |
|---|---|---|
| JP | 2005261817 A | 9/2005 |
| JP | 2005532086 A | 10/2005 |
| JP | 2010051596 A | 3/2010 |
| JP | 2011013503 A | 1/2011 |
| JP | 2012029869 A | 2/2012 |
| JP | 2014069070 A | 4/2014 |
| JP | 2015162760 A | 9/2015 |
| JP | 2018126205 A | 8/2018 |
| WO | 2005082314 A1 | 9/2005 |

\* cited by examiner

| Step | C1 (mmHg) | C2 (mmHg) | C3 (mmHg) | C4 (mmHg) | C5 (mmHg) | Duration (Seconds) |
|---|---|---|---|---|---|---|
| 0 | 0 | 0 | 0 | 35 | 15 | 60 |
| 1 | 30 | 45 | 30 | 15 | 15 | 30 |
| 2 | 45 | 45 | 45 | 15 | 15 | 30 |
| 3 | 50 | 50 | 50 | 15 | 15 | 60 |
| 4 | 50 | 0 | 50 | 15 | 15 | 60 |
| 5 | 20 | 0 | 20 | 15 | 15 | 60 |
| 6 | 30 | 45 | 30 | 15 | 15 | 60 |
| 7 | 45 | 50 | 45 | 15 | 15 | 60 |
| 8 | 0 | 45 | 45 | 15 | 15 | 60 |
| 9 | 45 | 45 | 0 | 15 | 15 | 60 |
| 10 | 45 | 45 | 45 | 15 | 15 | 60 |
| 11 | 45 | 0 | 45 | 15 | 15 | 60 |
| 12 | 45 | 0 | 45 | 15 | 15 | 60 |
| 13 | 30 | 30 | 30 | 15 | 15 | 60 |
| 14 | 30 | 20 | 30 | 15 | 15 | 120 |
| 15 | 20 | 0 | 20 | 15 | 15 | 60 |
| 16 | 20 | 30 | 20 | 15 | 15 | 60 |
| 17 | 30 | 20 | 30 | 15 | 15 | 60 |
| 18 | 20 | 20 | 20 | 15 | 15 | 60 |
| 19 | 20 | 0 | 20 | 15 | 15 | 60 |
| 20 | 20 | 20 | 20 | 15 | 15 | 60 |
| 21 | 30 | 30 | 30 | 15 | 15 | 60 |
| 22 | 20 | 20 | 20 | 15 | 15 | 60 |
| 23 | 20 | 20 | 20 | 15 | 15 | 60 |
| 24 | 20 | 0 | 20 | 15 | 15 | 60 |

Determine that a pressure-mitigation apparatus has been connected to a controller

1102

Identify a pattern corresponding to the pressure-mitigation apparatus

1103

Cause chambers of the pressure-mitigation apparatus to be inflated in accordance with the pattern

1104

Receive input indicative of a request to initiate a deflation procedure

1105

Cause deflation of a chamber, a side support, or any combination thereof

1201
Determine that a pressure-mitigation apparatus has been connected to a controller 1202
Identify a pattern corresponding to the pressure-mitigation apparatus 1203
Cause chambers of the pressure-mitigation apparatus to be inflated in accordance with the pattern 1204
Acquire pressure data representative of the values of electrical signals generated by transducer(s) mounted in the controller 1205
Examine the pressure data to identify movement(s) of the human body under which the pressure-mitigation apparatus is positioned 1206
Estimate a characteristic of the human body based on the pressure data, the movement(s), or any combination thereof

FIGURE 12

METHODS FOR CONTROLLING AND MONITORING INFLATABLE PERFUSION ENHANCEMENT APPARATUSES AND ASSOCIATED SYSTEMS

CROSS-REFERENCE TO RELATED APPLICATIONS

This application is a divisional of U.S. patent application Ser. No. 16/584,704, filed Sep. 26, 2019, which is a continuation-in part application of U.S. patent application Ser. No. 16/363,094, filed Mar. 25, 2019, which claims the benefit of U.S. Provisional Patent Application No. 62/736,758, filed on Sep. 26, 2018, U.S. Provisional Patent Application No. 62/690,206, filed Jun. 26, 2018, and U.S. Provisional Patent Application No. 62/647,551, filed Mar. 23, 2018, all of which are incorporated herein by reference in their entireties.

TECHNICAL FIELD

The present technology relates generally to apparatuses, systems, and methods for controlling and monitoring inflatable perfusion enhancement apparatuses that mitigate contact pressure applied to a human body by a support surface.

BACKGROUND

Pressure injuries (sometimes referred to as "decubitus ulcers," "pressure ulcers," "pressure sores," or "bedsores") typically occur as a result of steady pressure applied in one location along a surface of the human body such as, for example, the sacrum. Pressure injuries are most common in individuals who are mobility-impaired or immobilized (e.g., in a wheelchair or a bed, or on an operating table) for prolonged periods of time. Oftentimes these individuals are older, malnourished, and/or incontinent, all factors that predispose the human body to pressure injury formation. Because these individuals are often not ambulatory, they may sit or lie for prolonged periods of time in the same position. Moreover, these individuals often are unable to reposition themselves to alleviate the pressure. Consequently, the pressure on the skin and soft tissue eventually causes ischemia or inadequate blood flow to the area, thereby resulting in breakdown of the skin and tissue damage. Pressure injuries can result in a superficial injury to the skin, or a deeper full-thickness ulcer that exposes underlying tissues and places the individual at risk for infection. The resulting infection may worsen, leading to sepsis, or even death in some cases.

There are various pressure technologies on the market for preventing pressure injuries. However, conventional alternating pressure technologies have many deficiencies, including the inability to control the spatial relationship between an individual and a support surface. Consequently, individuals using conventional alternating pressure technologies may still develop pressure injuries or suffer from related complications.

BRIEF DESCRIPTION OF THE DRAWINGS

Many aspects of the present disclosure can be better understood with reference to the following drawings. The components in the drawings are not necessarily to scale. Instead, emphasis is placed on clearly illustrating the principles of the present disclosure. Furthermore, components may be shown as transparent in certain views for the purpose of illustration, rather than to indicate that the component is necessarily transparent. Any headings provided herein are for convenience only.

FIG. 10 is a table illustrating a sequence for inflating chambers of a pressure-mitigation apparatus in accordance with embodiments of the present technology.

FIG. 11 is a flow diagram of a process for varying the pressure in chambers of a pressure-mitigation apparatus in accordance with embodiments of the present technology.

FIG. 12 is a flow diagram of a process for establishing characteristics of a human body supported by a pressure-mitigation apparatus in accordance with embodiments of the present technology.

DETAILED DESCRIPTION

Figure 1A:
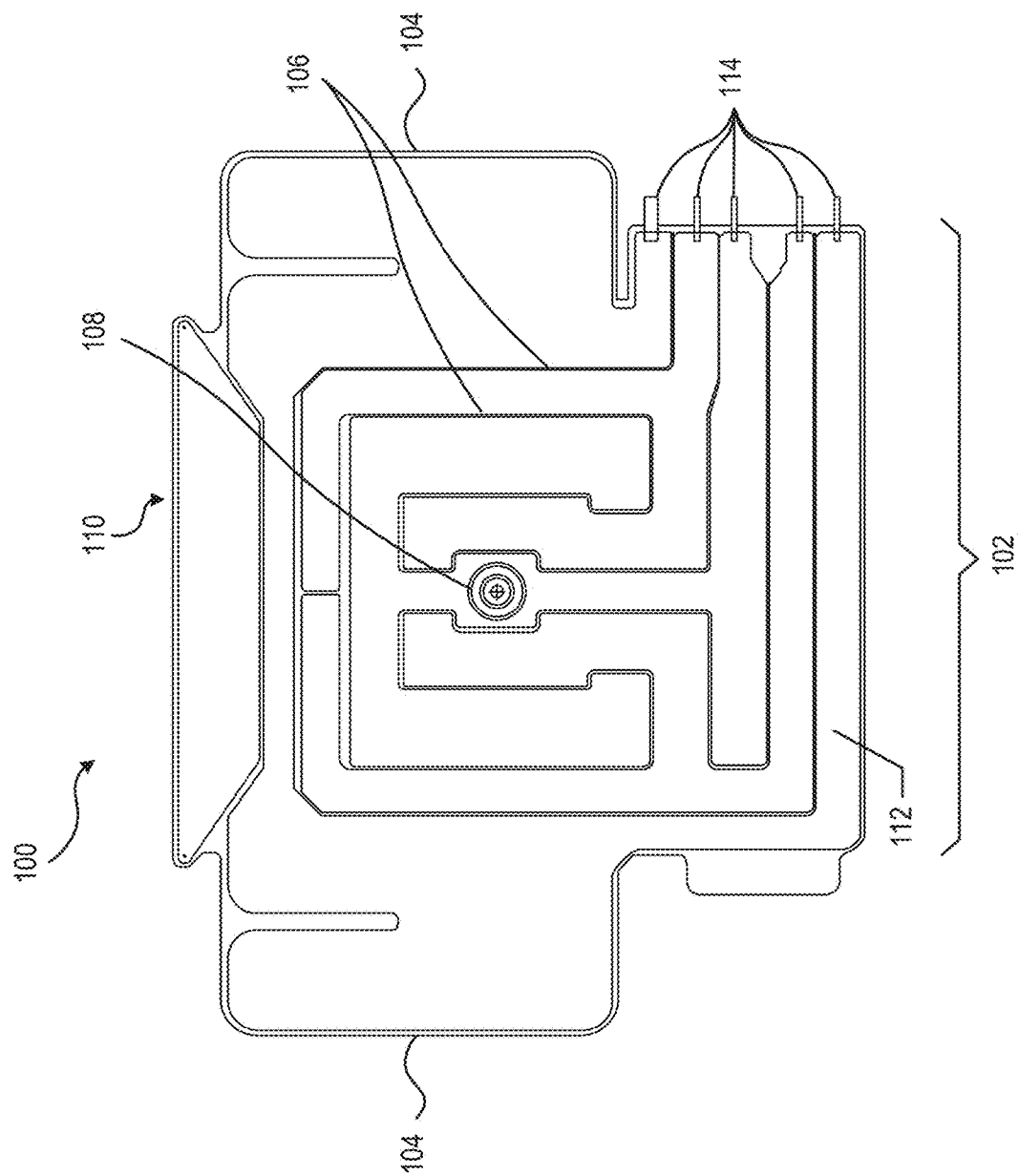
FIGS. 1A and 1B are top and bottom views, respectively, of a pressure-mitigation apparatus configured in accordance with embodiments of the present technology.

Pressure injuries (also referred to a "pressure ulcers" or "ulcers") are localized regions of damage to the skin and/or the underlying tissue that result from contact pressure (or simply "pressure") on the corresponding anatomical region of the body. Pressure injuries often form over bony prominences, such as the skin and soft tissue overlying the sacrum, coccyx, heels, or hips. However, other sites (e.g., the elbows, knees, ankles, shoulders, abdomen, back, or cranium) may also be affected. Generally, pressure injuries develop when pressure is applied to blood vessels in soft tissue, which at least partially obstructs blood flow to the soft tissue (e.g., when the pressure exceeds the capillary filling pressure) and causes ischemia at the pressure site for an extended duration. Therefore, pressure injuries often occur in individuals who are mobility-impaired, immobilized, or sedentary for prolonged periods of times. Once a pressure injury forms, the healing process is typically slow. For example, when pressure is relieved from the site of the pressure injury, the body rushes blood (including proinflammatory mediators) to that region to perfuse the area. The sudden reperfusion of the damaged, previously ischemic region has been shown to cause an inflammatory response, brought on by the proinflammatory mediators, that can actually worsen the original pressure injury and prolongs recovery. Further, depending on the patient and the pressure injury, the proinflammatory mediators may spread through the blood stream beyond the site of the pressure injury to cause a systematic inflammatory response. This secondary inflammatory response caused by the proinflammatory mediators has been shown to exacerbate existing conditions or trigger additional ailments, thereby slowing recovery. Moreover, recovery time can be prolonged by numerous factors often associated with individuals prone to pressure injuries, such as old age, immobility, preexisting medical conditions (e.g., arteriosclerosis, diabetes, or infection), smoking, and/or medications (e.g., anti-inflammatory drugs). Thus, preventing or reducing pressure injury formation (and reducing proinflammatory mediators) can enhance and expedite many treatment processes for individuals, especially those who are mobility-impaired during the course of treatment.

Introduced here, therefore, are systems and methods for controlling and monitoring inflatable perfusion enhancement apparatuses that mitigate contact pressure applied to a human body by a support surface. A controller device (also referred to as a "controller") can be fluidically coupled to a pressure-mitigation apparatus (also referred to as a "pressure-mitigation device" or a "pressure-mitigation pad") that includes a series of selectively inflatable chambers (also referred to as "cells"). When the pressure-mitigation apparatus is placed between a human body and a support surface (also referred to as a "contact surface"), the controller device can continuously and intelligently circulate air through the pressure mitigation apparatus. The controller device causes one or more chambers of the pressure-mitigation device to selectively inflate, deflate, or any combination thereof.

By controllably varying the pressure in the series of chambers, the controller device can move the main point of pressure applied by the support surface to various different regions across the human body. For example, following deployment of the pressure-mitigation apparatus, the controller device can move the main point(s) of pressure applied by the support surface amongst a plurality of predetermined locations by sequentially varying the level of inflation of and, therefore, pressure in different predetermined subsets of inflatable chambers. In some embodiments, the controller controls pressure beneath specific anatomic locations of the patient for specific durations in order to move pressure points around the anatomy in a precise manner such that specific portions of the anatomy (e.g., tissue adjacent bony prominences) have minimal pressure applied for predetermined periods of time. This continuous or intermittent relocation of the pressure point(s) avoids vascular compression for sustained periods of time and, therefore, inhibits ischemia and ultimately reduces the incidence of pressure injuries.

In addition, the controller device can provide various different features and functions that provide for and enhance dynamic control of the pressure-mitigation device. For example, the controller device may be configured to auto-detect the type of pressure-mitigation device attached thereto and configure the pressure mitigation inflation-deflation protocol for that type of device.

The controller device can also provide alerts to the patient, caregivers, and others related to the functionality of the pressure-mitigation device and patient monitoring (e.g., improper usage, compliance to treatment protocol). In some embodiments, for example, the controller device can also detect patient motion on the pressure mitigation device by remotely monitoring the pressures within the air chambers, and then use this information to determine information in real-time regarding patient movement and patient location on the device.

Specific details of several embodiments of the present technology are described herein with reference to FIGS. 1A-14. Although many of the embodiments are described herein with respect to systems, apparatuses, and methods for controlling inflatable perfusion enhancement apparatuses and associated systems and methods for alleviating the pressure applied to a human body (e.g., a patient, individual, or subject) in a certain position (e.g., the supine position) by a support surface (e.g., a mattress), other embodiments in addition to those described herein are within the scope of the present technology. For example, at least some embodiments of the present technology may be useful for alleviating the pressure applied to a human body in a sitting position. In such embodiments, the chambers of the pressure-mitigation apparatus may be different sizes, in different arrangements, and/or otherwise differ from the chambers of pressure-mitigation apparatuses for patients oriented in a supine position. Additionally, or alternatively, the chambers of the pressure-mitigation apparatus may be inflated in a different order, with different pressures, for different durations, and/or otherwise have a different inflation pattern than those of pressure-mitigation apparatuses for patients oriented in a supine position.

It should be noted that other embodiments in addition to those disclosed herein are within the scope of the present technology. For example, components, configurations, and/or procedures shown or described with respect to one embodiment can be combined with or replace the components, configurations, and/or procedures described in other embodiments. Further, embodiments of the present technology can have different components, configurations, and/or procedures than those shown or described herein. Moreover, a person of ordinary skill in the art will understand that embodiments of the present technology can have configurations, components, and/or procedures in addition to those shown or described herein, and that these and other embodiments can be without several of the configurations, components, and/or procedures shown or described herein without deviating from the present technology.

Selected Embodiments of Pressure-Mitigation Apparatuses

A pressure-mitigation apparatus includes a plurality of chambers or compartments that can be individually controlled to vary the pressure in each chamber and/or a subset of the chambers. When placed between a human body and a support surface, the pressure-mitigation apparatus can vary the pressure on an anatomical region by controllably inflating one or more chambers, deflating one or more chambers, or any combination thereof. Several examples of pressure-mitigation apparatuses are described below with respect to FIGS. 1A-3. Unless otherwise noted, any features described with respect to one embodiment are equally applicable to the other embodiments. Some features have only been described with respect to a single embodiment of the pressure-mitigation apparatus for the purpose of simplifying the present disclosure.

Figure 1B:
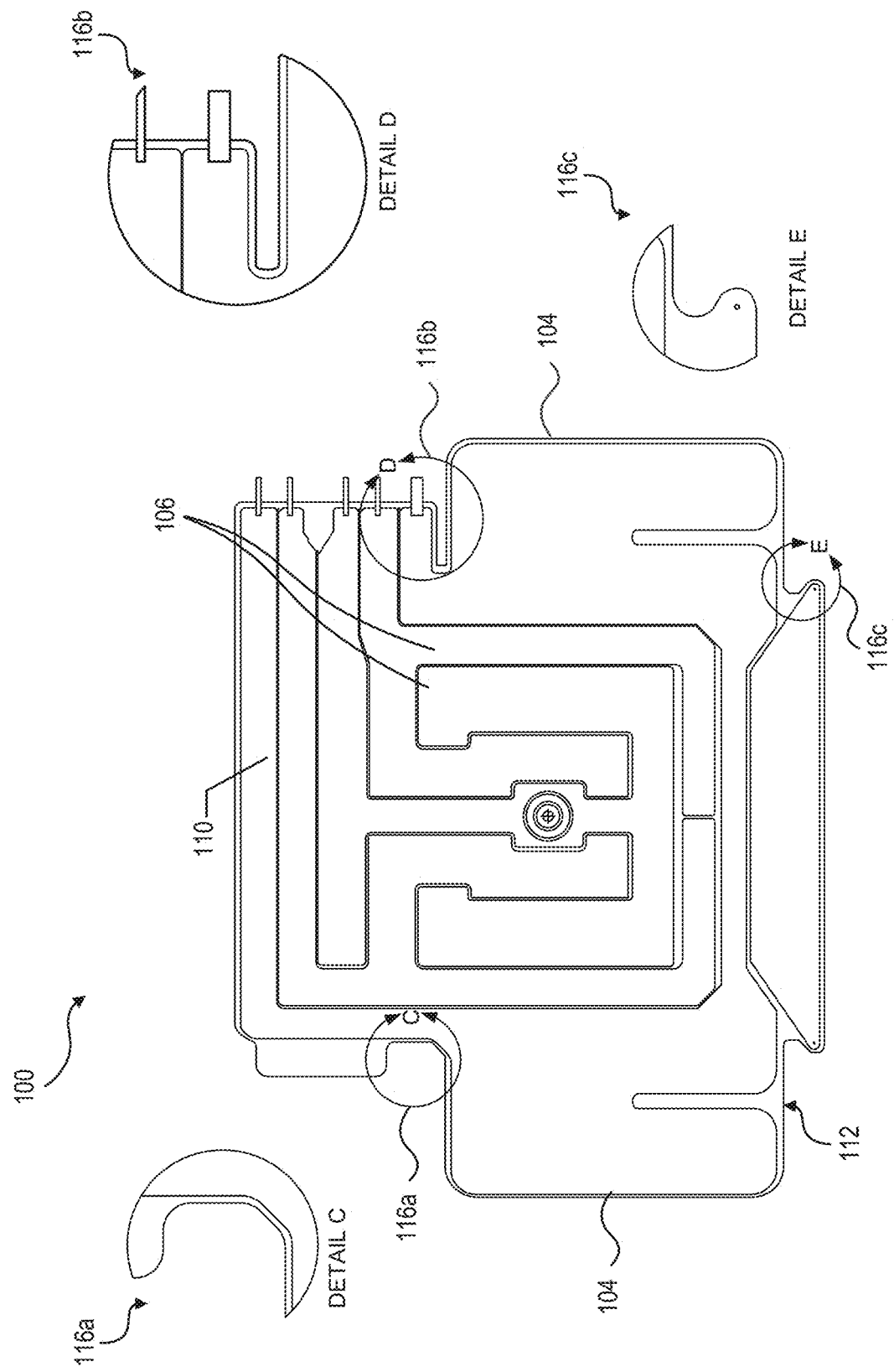

FIGS. 1A and 1B are top and bottom views, respectively, of a pressure-mitigation apparatus 100 for relieving pressure on a specific anatomical region applied by an elongated support surface in accordance with embodiments of the present technology. The pressure-mitigation apparatus 100 can be used in conjunction with elongated support surfaces, such as mattresses, stretchers, operating tables, and procedure tables. In some embodiments the pressure-mitigation apparatus 100 is secured to a support surface using an attachment apparatus, while in other embodiments the pressure-mitigation apparatus 100 is placed in direct contact with the support surface (i.e., without any attachment apparatus therebetween).

As shown in FIG. 1A, the pressure-mitigation apparatus 100 can include a central portion 102 (also referred to as a "contact portion") positioned alongside at least one side support 104. Here, a pair of side supports 104 are arranged on opposing sides of the central portion 102. However, some embodiments of the pressure-mitigation apparatus 100 do not include any side supports. For example, the side support(s) 104 may be omitted when the individual is medically immobilized (e.g., under anesthesia, in a medically induced coma, etc.) and/or physically restrained by the underlying support surface (e.g., by rails along the side of a bed, armrests along the side of a chair) and/or other structures (e.g., physical restraints holding down the patient, casts, etc.).

The pressure-mitigation apparatus 100 includes a series of chambers 106 (also referred to as "cells") whose pressure can be individually varied. In some embodiments, the series of chambers 106 are arranged in a geometric pattern designed to relieve pressure on one or more specific anatomical regions of a human body. As noted above, when placed between the human body and a support surface, the pressure-mitigation apparatus 100 can vary the pressure on the specific anatomical region(s) by controllably inflating chamber(s), deflating chamber(s), or any combination thereof.

In some embodiments, the geometric pattern is designed to mitigate pressure on a specific anatomical region when the specific anatomical region is oriented over a target region 108 of the geometric pattern. As shown in FIGS. 1A and 1B, the target region 108 may represent a central point or portion of the pressure-mitigation apparatus 100 to appropriately position the person's anatomy with respect to the pressure-mitigation apparatus 100. For example, the target region 108 may correspond to an epicenter of the geometric pattern. However, the target region 108 may not necessarily be the central point of the pressure-mitigation apparatus 100, particularly if the pressure-mitigation apparatus 100 is not symmetric. The target region 108 may be marked so that an individual (e.g., a physician, nurse, caregiver, or the patient himself or herself) can readily align the target region 108 with a corresponding anatomical region of the human body to be positioned thereon.

The pressure-mitigation apparatus 100 can include a first portion 110 (also referred to as a "first layer" or a "bottom layer") designed to face a support surface and a second portion 112 (also referred to as a "second layer" or a "top layer") designed to face the human body supported by the support surface. In some embodiments the first portion 110 is directly adjacent to the support surface, while in other embodiments the first portion 110 is directly adjacent to an attachment apparatus designed to help secure the pressure-mitigation apparatus 100 to the support surface. The pressure-mitigation apparatus 100 may be constructed of a variety of materials, and the material(s) used in the construction of each component of the pressure-mitigation apparatus 100 may be chosen based on the nature of the body contact, if any, to be experienced by the component. For example, because the second portion 112 will often be in direct contact with the skin, it may be comprised of a soft fabric or a breathable fabric (e.g., comprised of moisture-wicking materials or quick-drying materials, or having perforations). In some embodiments, an impervious lining (e.g., comprised of polyurethane) is secured to the inside of the second portion 112 to inhibit fluid (e.g., sweat) from entering the series of chambers 106. As another example, if the pressure-mitigation apparatus 100 is designed for deployment beneath a cover (e.g., a bed sheet), then the second portion 112 may be comprised of a liquid-impervious, flexible material, such as polyurethane, polypropylene, silicone, or rubber. The first portion 110 may also be comprised of a liquid-impervious, flexible material.

The series of chambers 106 may be formed via interconnections between the first and second portions 110, 112 (e.g., either directly or via one or more intermediary layers). In the embodiment illustrated in FIGS. 1A and 1B, the pressure-mitigation apparatus 100 includes an "M-shaped" chamber intertwined with two "C-shaped" chambers that face one another. Such an arrangement has been shown to effectively mitigate the pressure applied to the sacral region of a human body in the supine position by a support surface when the pressure in these chambers is alternated. A pressure-mitigation apparatus may have another arrangement of chambers if the pressure-mitigation apparatus is designed for an anatomical region other than the sacral region, or if the pressure-mitigation apparatus is to be used to support a human body in a non-supine position (e.g., a sitting position). Generally, the geometric pattern of the chambers 106 is designed based on the internal anatomy (e.g., the muscles, bones, and vasculature) of a specific anatomical region on which pressure is to be relieved.

The person using the pressure-mitigation apparatus 100 and/or the caregiver (e.g., a nurse, physician, etc.) will often be responsible for actively orienting the anatomical region of the patient lengthwise over the target region 108 of the geometric pattern. However, the side support(s) 104 may actively orient or guide the specific anatomical region of the human body laterally over the target region 108 of the geometric pattern. In some embodiments the side support(s) 104 are inflatable, while in other embodiments the side support(s) 104 are permanent structures that protrude from one or both lateral sides of the pressure-mitigation device 100. For example, at least a portion of each side support may be stuffed with cotton, latex, polyurethane foam, or any combination thereof.

As further described below with respect to FIGS. 6A and 6B, a controller device can separately control the pressure in each chamber (as well as the side supports 104, if included) by providing a discrete airflow via one or more corresponding valves 114. In some embodiments, the valves 114 are permanently secured to the pressure-mitigation apparatus 100 and designed to interface with tubing that can be readily detached (e.g., for easier transport, storage, etc.). Here, the pressure-mitigation apparatus 100 includes five valves 114.

Three valves are fluidically coupled to the series of chambers 106, and two valves are fluidically coupled to the side supports 104. In other embodiments, the pressure-mitigation apparatus 100 includes more than five valves 114 and/or less than five valves 114.

In some embodiments, the pressure-mitigation apparatus 100 includes one or more structural feature(s) 116a-c that enhance securement of the pressure-mitigation apparatus 100 to a support surface and/or an attachment apparatus. As illustrated in FIG. 1B, for example, the pressure-mitigation apparatus 100 can include three design feature(s) 116a-c, each of which can be aligned with a corresponding structural feature that is accessible along the support surface or the attachment apparatus. For example, each design feature 116a-c may be designed to at least partially envelope a structural feature that protrudes upward. The design feature(s) 116a-c may also facilitate proper alignment of the pressure-mitigation apparatus 100 with the support surface or the attachment apparatus.

Figure 2A:
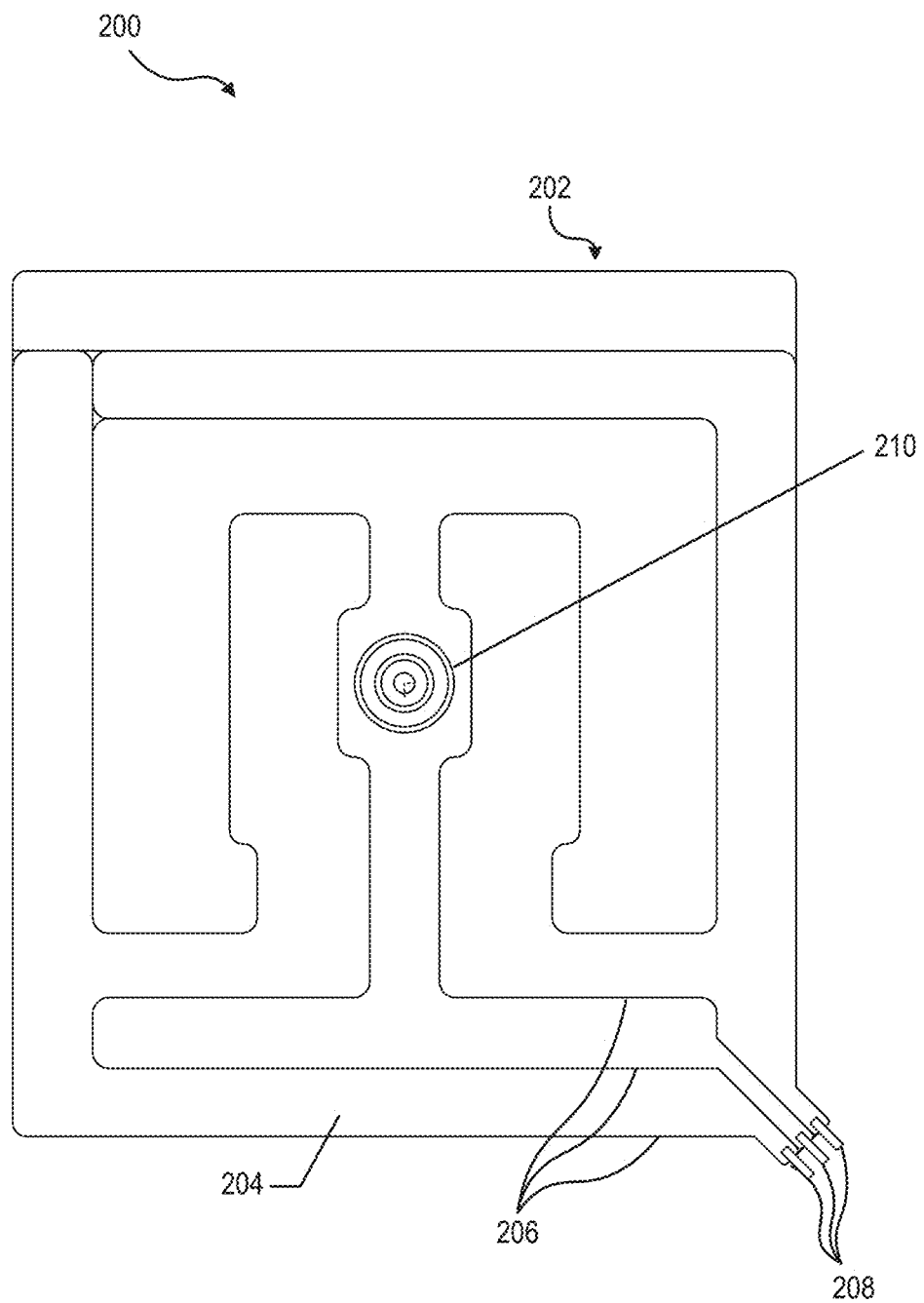
FIGS. 2A and 2B are top and bottom views, respectively, of a pressure-mitigation apparatus configured in accordance with embodiments of the present technology.
Figure 2B:
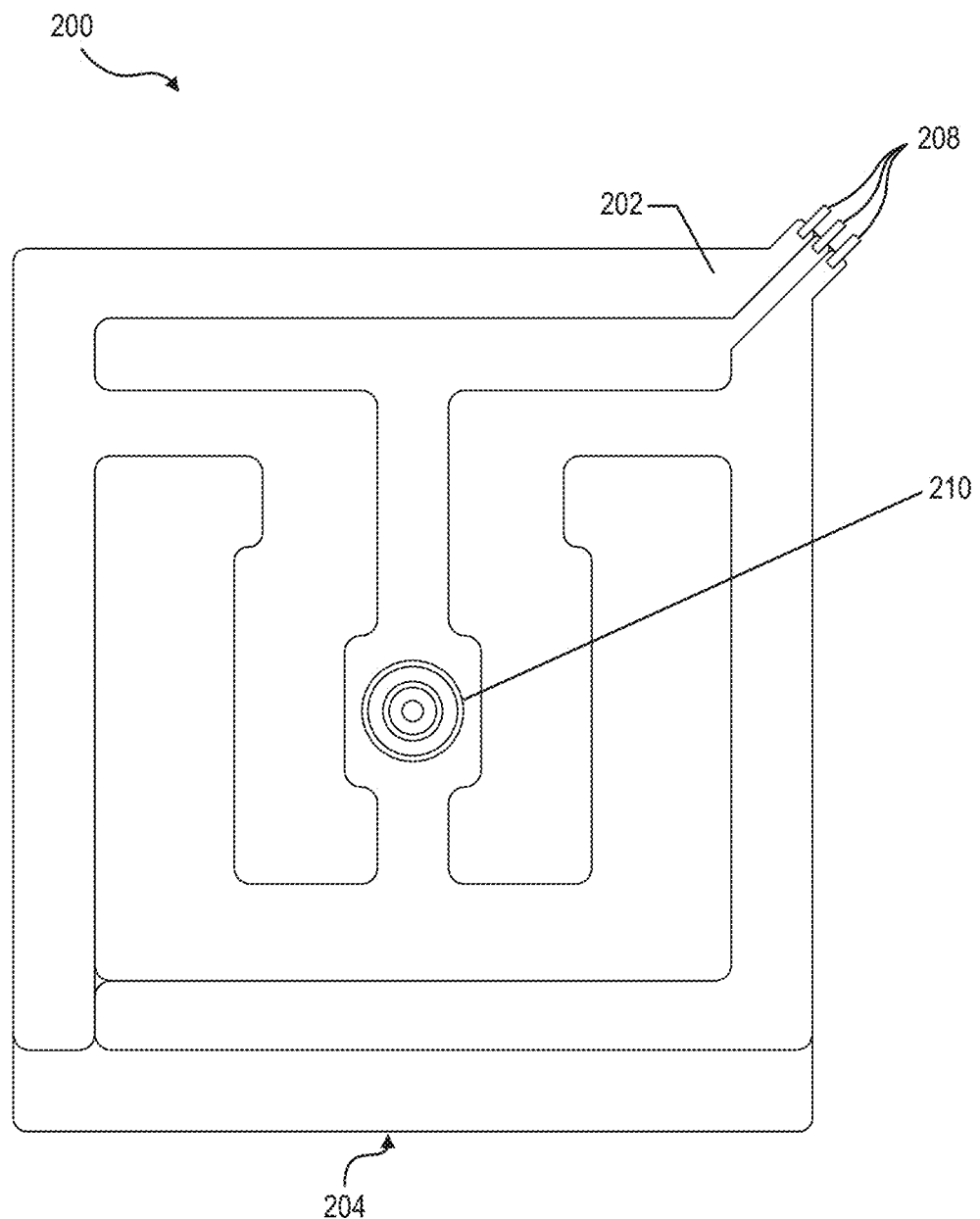

FIGS. 2A and 2B are top and bottom views, respectively, of a pressure-mitigation apparatus 200 configured in accordance with embodiments of the present technology. The pressure-mitigation apparatus 200 is generally used in conjunction with nonelongated support surfaces that support individuals in a seated or partially erect position, such as chairs (e.g., office chairs, examination chairs, recliners, and wheelchairs) and the seats included in vehicles and airplanes. As such, the pressure-mitigation apparatus 200 will often be positioned atop support surfaces that have side supports integrated into the support itself (e.g., the side arms of a recliner or wheelchair). In some embodiments the pressure-mitigation apparatus 200 is secured to a support surface using an attachment apparatus, while in other embodiments the attachment apparatus is omitted such that the pressure-mitigation apparatus 200 directly contacts the underlying support surface.

The pressure-mitigation apparatus 200 can include various features generally similar to the features of the pressure-mitigation device 100 described above with respect to FIGS. 1A and 1B. For example, the pressure-mitigation apparatus 200 may include a first portion 202 (also referred to as a "first layer" or a "bottom layer") designed to face the support surface, a second portion 204 (also referred to as a "second layer" or a "top layer") designed to face the human body supported by the support surface, and a plurality of chambers 206 formed via interconnections between the first and second portions 202, 204. In this embodiment, the pressure-mitigation apparatus 200 includes an "M-shaped" chamber 206 intertwined with a backward "J-shaped" chamber 206 and a backward "C-shaped" chamber 206. The alternating inflation/deflation of such an arrangement of chambers 206 has been shown to effectively mitigate the pressure applied by a support surface to the sacral region when the human body is in a seated position.

The individual inflation/deflation of these chambers 206 can be performed in a predetermined pattern and to predetermined pressure levels. In some embodiments, for example, the individual chambers 206 can be inflated to higher pressure levels than the chambers 206 of the pressure-mitigation apparatus 100 described with respect to FIGS. 1A and 1B because the human body supported by the pressure-mitigation apparatus 200 is in a seated position, thereby applying more pressure on the pressure-mitigation apparatus 200 than if the human body were supine or prone. Further, unlike the pressure mitigation device 100 of FIGS. 1A and 1B, the pressure-mitigation apparatus 200 of FIGS. 2A and 2B does not include side supports. As noted above, side supports may be omitted when the structure on which the individual is seated or reclined already provides components that laterally center the individual (e.g., rails along the side of a bed, armrests along the side of a chair), as is often the case with nonelongated support surfaces.

As further described below with respect to FIGS. 6A and 6B, a controller device can control the pressure in each chamber 206 by providing a discrete airflow via one or more corresponding valves 208. Here, the pressure-mitigation apparatus 200 includes three valves 208, and each of the three valves 208 corresponds to a single chamber 206. In other embodiments, the pressure-mitigation apparatus 200 may include one valve, two valves, or more than three valves 208, and each valve 208 can be associated with a specific chamber for individually controlled inflation and/or deflation of that chamber 206. In these and other embodiments, a single valve 208 can be fluidically coupled to two or more chambers 206. In these and other embodiments, a single chamber 206 can be in fluid communication with two or more valves 208 (e.g., one valve for inflation and another valve for deflation).

Figure 3:
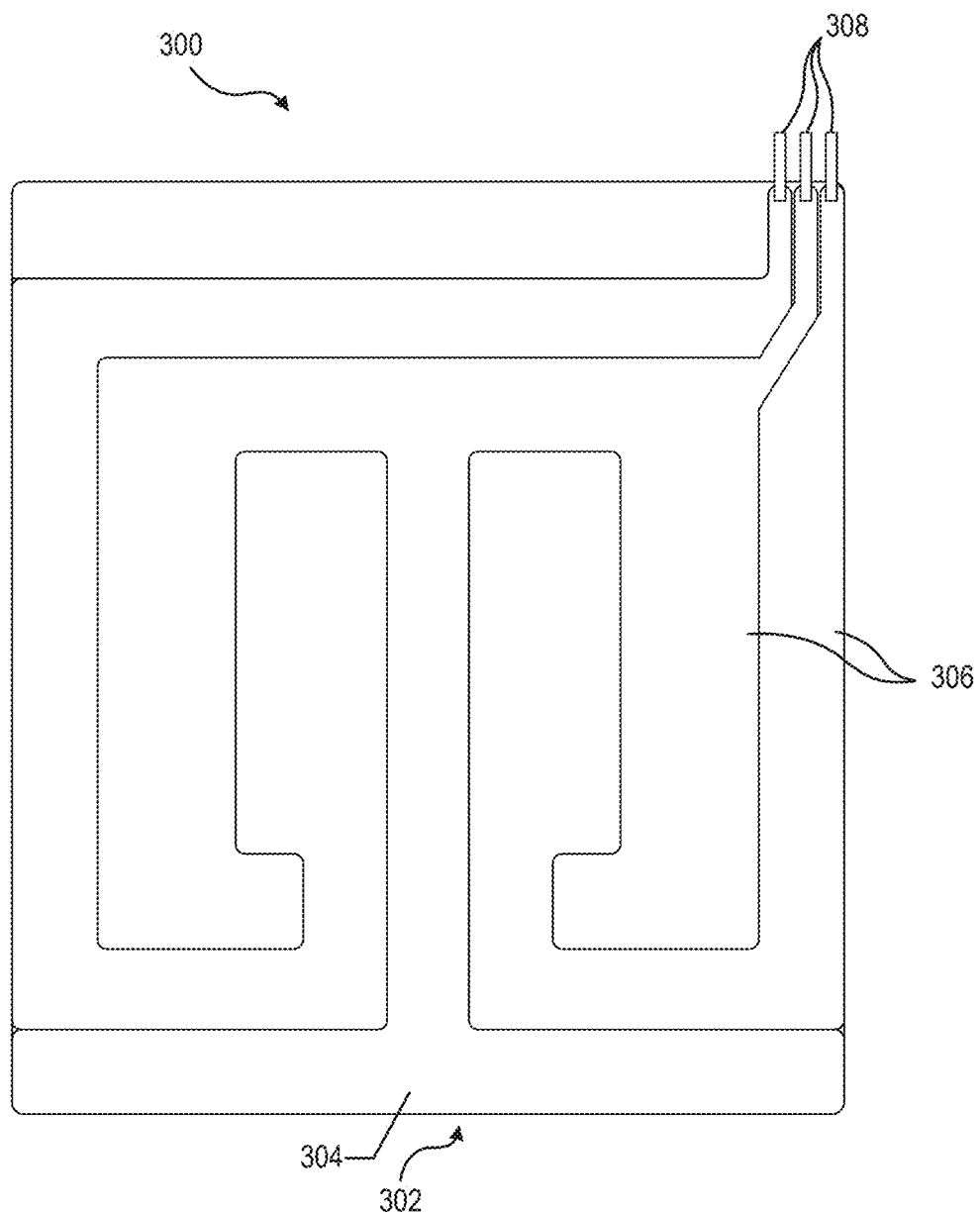
FIG. 3 is a top view of a pressure-mitigation apparatus configured in accordance with embodiments of the present technology.

FIG. 3 is a top view of a pressure-mitigation apparatus 300 for relieving pressure on a specific anatomical region applied by a wheelchair in accordance with embodiments of the present technology. The pressure-mitigation apparatus 300 can include various features generally similar to the features of the pressure-mitigation apparatus 200 of FIGS. 2A and 2B and the pressure-mitigation apparatus 100 of FIGS. 1A and 1B described above. For example, the pressure-mitigation apparatus 300 can include a first portion 302 (also referred to as a "first layer" or a "bottom layer") designed to face the seat of the wheelchair (i.e., the support surface), a second portion 304 (also referred to as a "second layer" or a "top layer") designed to face the human body supported by the seat of the wheelchair, a plurality of chambers 306 formed by interconnections between the first and second portions 302, 304, and a plurality of valves 308 that control the flow of fluid into and/or out of the chambers 306. In some embodiments the first portion 302 is directly adjacent to the seat of the wheelchair, while in other embodiments the first portion 302 is directly adjacent to an attachment apparatus. As shown in FIG. 3, the pressure-mitigation apparatus 300 may include an "M-shaped" chamber 306 intertwined with a "U-shaped" chamber 306 and a "C-shaped" chamber 306, which are inflated and deflated in accordance with a predetermined pattern to mitigate the pressure applied to the sacral region of a human body in a sitting position on the seat of a wheelchair.

Figure 4:
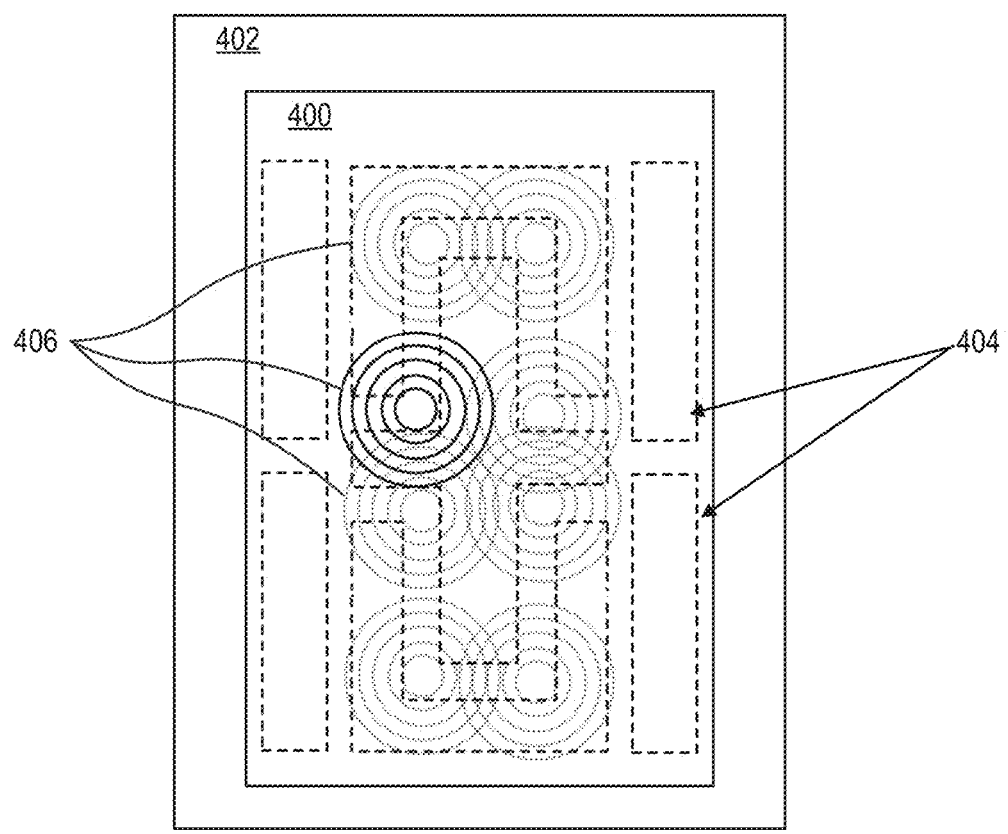
FIG. 4 is a partially schematic top view of a pressure-mitigation apparatus illustrating varied pressure distributions for avoiding ischemia for a mobility-impaired patient in accordance with embodiments of the present technology.

FIG. 4 is a partially schematic top view of a pressure-mitigation apparatus 400 illustrating varied pressure distributions for avoiding ischemia for a mobility-impaired patient in accordance with embodiments of the present technology. As discussed above, when a human body is supported by a contact surface 402 for an extended duration, pressure injuries may form in tissue overlaying bony prominences, such as the skin overlying the sacrum, coccyx, heels, or hips. These bony prominences often represent the location or locations at which the most pressure is applied by the contact surface 402 and, therefore, may be referred to as the "main pressure point(s)" along the surface of the human body. To prevent the formation of pressure injuries, healthy individuals periodically make minor positional adjustments (also known as "micro-adjustments") to shift the location of the main pressure point. However, individuals having impaired mobility often cannot make these micro-adjustments by themselves. Mobility impairment may be due to physical injury (e.g., a traumatic injury or a progressive injury), movement limitations (e.g., within a vehicle, on an aircraft, or in restraints), medical procedures (e.g., those requiring anesthesia), and/or other conditions that limit an individual's natural movement. For these mobility-impaired individuals, the pressure-mitigation apparatus 400 can be used to shift the location of the main pressure point(s) on their behalf. That is, the pressure mitigation apparatus 400 can create moving pressure gradients to avoid sustained, localized vascular compression and enhance tissue perfusion As shown in FIG. 4, the pressure-mitigation apparatus 400 can include a series of chambers 404 (also referred to as "cells") whose pressure can be individually varied. The chambers 404 may be formed by interconnections between a first or bottom layer and a second or top layer of the pressure-mitigation apparatus 400. The top layer may be comprised of a first material (e.g., an air-permeable, non-irritating material) configured for direct contact with a human body, while the bottom layer may be comprised of a second material (e.g., a non-air-permeable, gripping material) configured for direct contact with the contact surface 402 or an attachment apparatus. In these and other embodiments, the top layer and/or the bottom layer can be comprised of more than one material, such as a coated fabric or a stack of interconnected materials.

A pump, such as the pressure device 1314 described below with respect to FIG. 13, can be fluidically coupled to each chamber 404 (e.g., via a corresponding inlet valve), while a controller, such as the controller 1312 described below with respect to FIG. 13, can control the flow of fluid (e.g., air) generated by the pump into each chamber 404 on an individual basis in accordance with a predetermined pattern. As further described below, the pump and controller can operate the series of chambers 404 in several different ways. In some embodiments, the chambers 404 have a naturally deflated state, and the controller causes the pump to inflate at least one of the chambers 404 to shift the main pressure point along the anatomy of the user. For example, the pump may inflate at least one of the chambers 404 located directly beneath an anatomical region to momentarily apply contact pressure to that anatomical region and relieve the contact pressure on the surrounding anatomical regions adjacent to the deflated chamber(s) 404. In these and other implementations, the controller may cause the pump to inflate two or more chambers 404 adjacent to an anatomical region to create an open space or void beneath the anatomical region to shift the main pressure point at least momentarily away from the anatomical region. In other embodiments, the chambers 404 have a naturally inflated state, and the controller causes the pump to deflate at least one of the chambers 404 to shift the main pressure point along the anatomy of the user. For example, the pump may be configured to deflate at least one of the chambers 404 located directly beneath an anatomical region, thereby forming a void beneath the anatomical region to momentarily relieve the contact pressure on the anatomical region. Whether configured in a naturally deflated state or a naturally inflated state, the continuous or intermittent alteration of the inflation levels of the individual chambers 404 moves the location of the main pressure point across different portions of the human body. As shown in FIG. 4, for example, inflating and/or deflating the chambers 404 creates temporary contact regions 406 that move across the pressure-mitigation apparatus 400 in a predetermined pattern, and thereby change the location of the main pressure point(s) on the human body for finite intervals of time. Thus, the pressure-mitigation apparatus 400 can simulate the micro-adjustments made by mobile individuals to relieve stagnant pressure application caused by the contact surface 402.

As noted above, the series of chambers 404 may be arranged in an anatomy-specific pattern so that when the pressure within one or more individual chambers is altered, the contact pressure on a specific anatomical region of the human body is relieved (e.g., by shifting the main pressure point elsewhere). As shown in FIG. 4, for example, the main pressure point can be moved between eight different locations corresponding to the eight temporary contact regions 406. In some embodiments the main pressure point shifts between these locations in a predictable manner (e.g., in a clockwise or counter-clockwise pattern), while in other embodiments the main pressure point shifts between these locations in an unpredictable manner (e.g., in accordance with a random pattern, a semi-random pattern, and/or detected pressure levels). Those skilled in the art will recognize that the quantity and position of these temporary contact regions 406 may vary based on the arrangement of the series of chambers 404, the anatomical region supported by the pressure-mitigation apparatus 400, the characteristics of the human body supported by the pressure mitigation apparatus 400, and/or the condition of the user (e.g., whether the user is completely immobilized, partially immobilized, etc.).

In some embodiments, the pressure-mitigation apparatus 400 does not include side supports because the condition of the user (also referred to as a "patient") may not benefit from the positioning provided by the side supports. For example, side supports can be omitted when the patient is medically immobilized (e.g., under anesthesia, in a medically induced coma, etc.) and/or physically restrained by the underlying support surface (e.g., rails along the side of a bed, arm rests on the side of a chair) and/or other structures (e.g., physically restraints holding down the patient, casts, etc.).

Figure 5A:
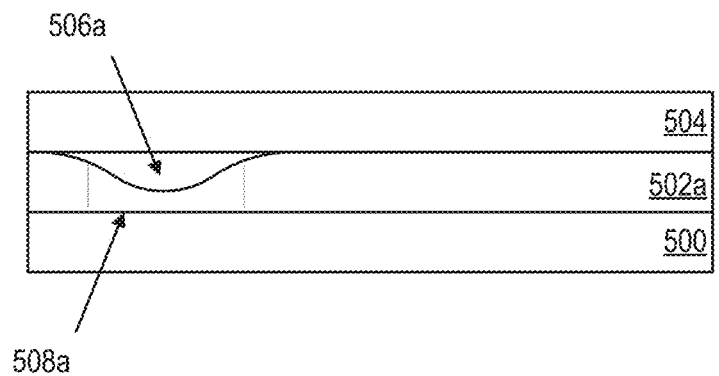
FIG. 5A is a partially schematic side view of a pressure-mitigation apparatus for relieving pressure on a specific anatomical region by chamber deflation in accordance with embodiments of the present technology.

FIG. 5A is a partially schematic side view of a pressure-mitigation apparatus 502a for relieving pressure on a specific anatomical region by chamber deflation in accordance with embodiments of the present technology. The pressure-mitigation apparatus 502a can be positioned between a contact surface 500 (e.g., a bed, table, or chair) and a human body 504 and, to relieve pressure on a specific anatomical region of the human body 504, at least one chamber 508a of a plurality of chambers (referred to collectively as "chambers 508") proximate to the specific anatomical region at least partially deflates to create an open region or void 506a beneath the specific anatomical region. In such embodiments, the remaining chambers 508 may remain inflated. Thus, the pressure-mitigation apparatus 502a may sequentially deflate chambers 508 (or arrangements of multiple chambers) to relieve the contact pressure applied to the human body 504 by the contact surface 500.

Figure 5B:
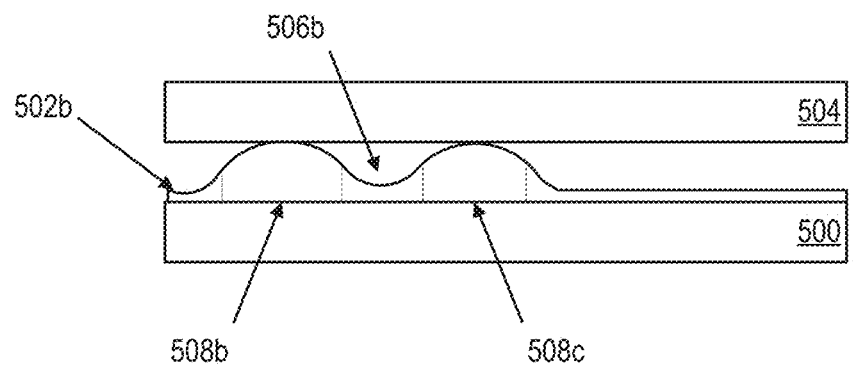
FIG. 5B is a partially schematic side view of a pressure-mitigation apparatus for relieving pressure on a specific anatomical by chamber inflation in accordance with embodiments of the present technology.

FIG. 5B is a partially schematic side view of a pressure-mitigation apparatus 502b for relieving pressure on a specific anatomical by chamber inflation in accordance with embodiments of the present technology. For example, to relieve pressure at a specific anatomical region of the human body 504, the pressure-mitigation apparatus 502b can inflate two chambers 508b and 508c disposed directly adjacent to the specific anatomical region to create a void 506b beneath the specific anatomical region. In such embodiments, the remaining chambers may remain at least partially deflated. Thus, the pressure-mitigation apparatus 502b may sequentially inflate a chamber (or arrangements of multiple chambers) to relieve the contact pressure applied to the human body 504 by the contact surface 500.

The pressure-mitigation apparatuses 502a and 502b of FIGS. 5A and 5B are shown to be in direct contact with the contact surface 500. However, in some embodiments, an attachment apparatus is positioned between the pressure-mitigation apparatuses 502a and 502b and the contact surface 500.

In some embodiments, the pressure-mitigation apparatuses 502a and 502b of FIGS. 5A and 5B can have the same configuration of chambers 508, and can operate in both a normally inflated state (described with respect to FIG. 5A) and a normally deflated state (described with respect to FIG. 5B) based on the selection of the operator (e.g., a medical professional or the user). For example, the operator can use a controller to select a normally deflated mode such that the pressure-mitigation device operates as described with respect to FIG. 5A, and then change the mode of operation to a normally inflated mode such that the pressure-mitigation device operates as described with respect to FIG. 5B. Thus, the pressure-mitigation apparatuses disclosed herein can shift the location of the main pressure point by controllably inflating the chambers, controllably deflating the chambers, or a combination thereof.

Selected Embodiments of Controller Devices

Figure 6A:
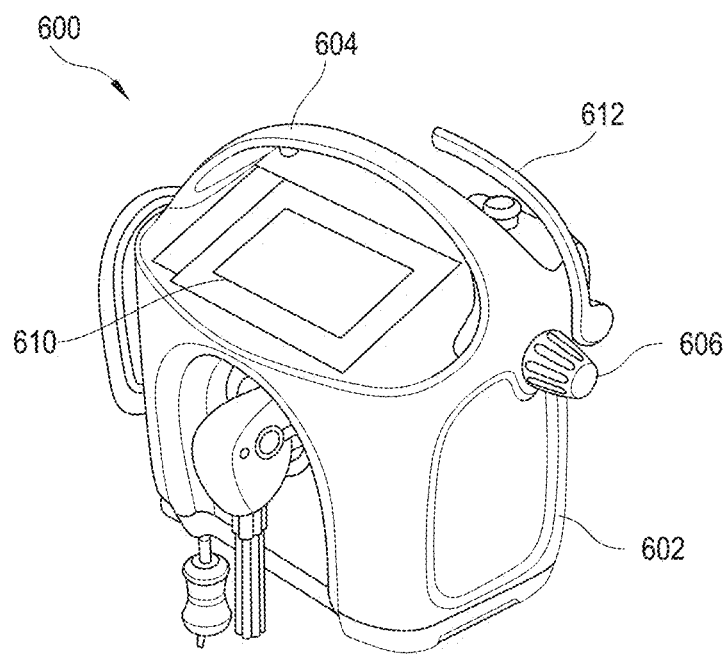
FIGS. 6A-6C are isometric, front, and back views, respectively, of a controller device (for initiating chamber inflation and/or deflation for a pressure-mitigation device in accordance with embodiments of the present technology.
Figure 6B:
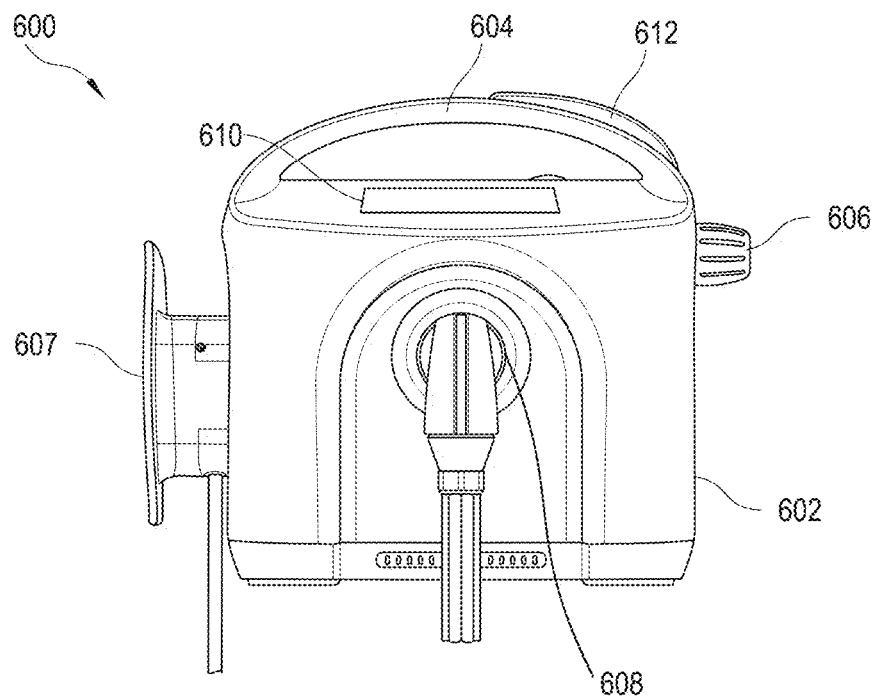
Figure 6C:
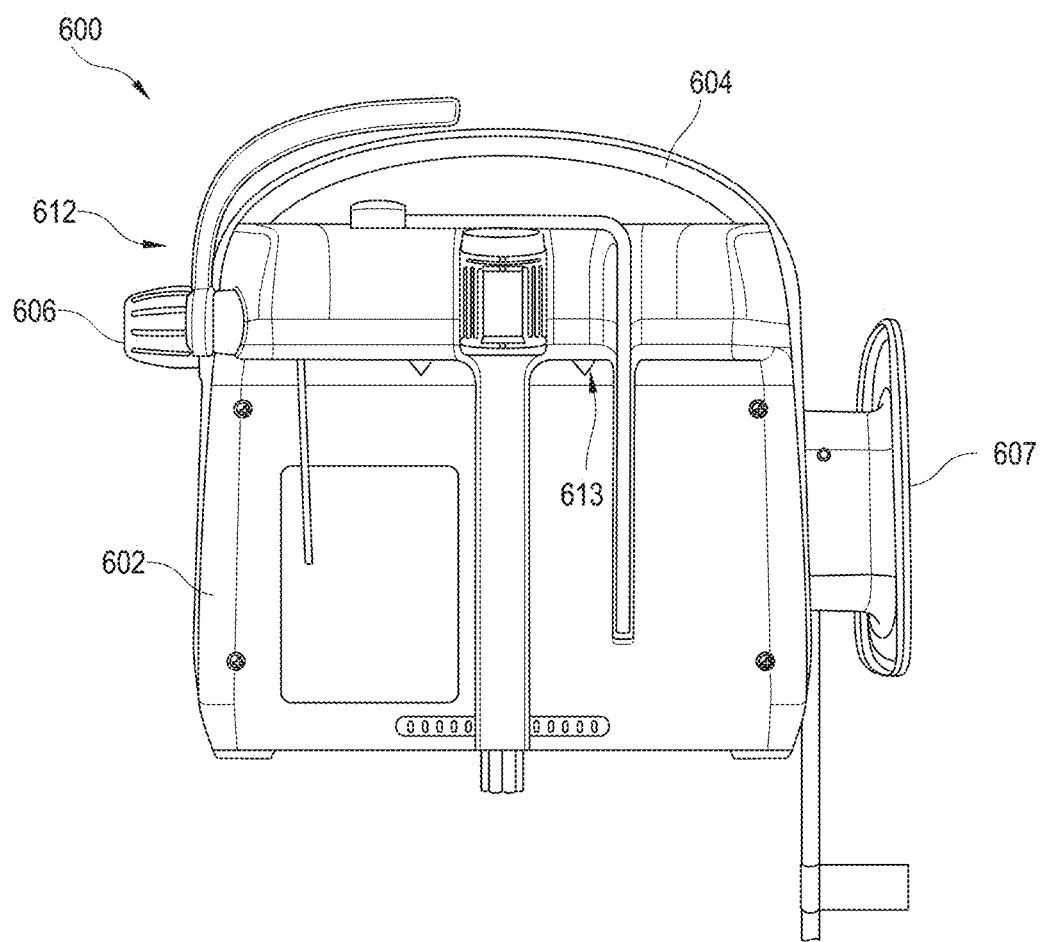

FIGS. 6A-6C are isometric, front, and back views, respectively, of a controller device 600 (also referred to as "the controller 600") for initiating chamber inflation and/or deflation of a pressure-mitigation device in accordance with embodiments of the present technology. For example, the controller 600 can be coupled to the pressure-mitigation apparatuses 100, 200, 300 described above with respect to FIGS. 1A-3 to control the pressure within the chambers 106, 206, 306. The controller 600 can manage the pressure in each chamber of a pressure-mitigation apparatus by controllably driving one or more pumps. In some embodiments, a single pump is fluidically connected to all the chambers such that the pump is responsible for directing fluid flow to and/or from multiple chambers. In other embodiments, the controller 600 is coupled to two or more pumps, each of which can be fluidically coupled to a single chamber to drive inflation/deflation of that chamber. In other embodiments, the controller 600 is coupled to at least one pump that is fluidically coupled to two or more chambers and/or at least one pump that is fluidically coupled to a single chamber. The pump(s) can reside within the same housing as the controller itself such that the system is easily transportable. Alternatively, the one or more pumps may reside in a housing separate from the controller.

As shown in FIGS. 6A-6C, the controller 600 can include a housing 602 in which internal components (e.g. those described below with respect to FIG. 7) reside and a handle 604 connected to the housing 602. In some embodiments the handle 604 is fixedly secured to the housing 602 in a predetermined orientation, while in other embodiments the handle 604 is pivotably secured to the housing 602. For example, the handle 604 may be configured to rotate about a hinge connected to the housing between multiple positions. The hinge may be one of a pair of hinges connected to the housing 602 along opposing lateral sides. In some embodiments, the controller device 600 can include cord retention mechanism 607 that is attached to or integrated with the housing 606. Cords (e.g., electrical cords), tubes, and/or other elongated structures associated with the system can be wrapped around or otherwise supported by the cord retention mechanism 607. Thus, the cord retention mechanism 607 can provide strain relief and retention of the power cord and, in certain embodiments, can also provide a flexible flange that retains the power cord plug.

As further shown in FIGS. 6A-6C, the controller 600 may include a connection mechanism 612 that allows the housing 602 to be securely, yet releasably, attached to a structure (e.g., of a mobile cart, bedframe, rail, table). In the illustrated embodiment, the connection mechanism 612 is a mounting hook that allows for single hand operation and is adjustable to allow for attachment to mounting surfaces with various thicknesses. In some embodiments, the controller device 600 can include an integrated intravenous (IV) pole clamp 613 that eases attachment of the controller device 600 to IV poles. The IV pole clamp may provide for quick activation and can be self-centering with the use of a single activation mechanism (e.g., knob or button).

In some embodiments, the housing 602 includes one or more mechanical input components 606 for providing instructions to the controller 600. The input components 606 may include one or more knobs (e.g., as shown in FIGS. 6A-6C), dials, buttons, levers, and/or other actuation mechanisms. An operator can interact with the one or more input components 606 to alter airflow provided to the pressure-mitigation apparatus, discharge air from the pressure-mitigation apparatus, or disconnect the controller 600 from the pressure-mitigation apparatus (e.g., by disconnecting the controller 600 from tubing connected between the controller 600 and the pressure-mitigation apparatus).

As further described below, the controller 600 can be configured to inflate and/or deflate the individual chambers of a pressure-mitigation apparatus in a predetermined pattern. In some embodiments at least one pressure device (e.g., an air pump) resides in the housing 602 of the controller 600, while in other embodiments the controller 600 is fluidically connected to at least one pressure device. For example, the housing 602 may include a first fluid interface through which fluid is received from pressure device(s) and a second fluid interface through which fluid is directed to the pressure-mitigation apparatus. Multi-channel tubing may be connected to one or both of these fluid interfaces. For example, multi-channel tubing may be connected between the first fluid interface of the controller 600 and multiple pressure devices. As another example, multi-channel tubing may be connected between the second fluid interface of the controller 600 and multiple valves of the pressure-mitigation apparatus. Here, the controller 600 includes a fluid interface 608 designed to interface with a multi-channel tubing. In some embodiments the multi-channel tubing permits unidirectional fluid flow, while in other embodiments the multi-channel tubing permits bidirectional fluid flow. Thus, fluid returning from the pressure-mitigation apparatus (e.g., as part of a discharge process) may travel back to the controller 600 through the second fluid interface. By controlling the exhaust of fluid returning from the pressure-mitigation apparatus, the controller 600 can actively manage noise created during use.

By monitoring the connection with the fluid interface 608, the controller 600 may be able to detect which type of pressure-mitigation apparatus has been connected. Each type of pressure-mitigation apparatus may include a different type of connector. For example, the pressure-mitigation apparatus designed for elongated support surfaces (e.g., pressure-mitigation apparatus 100 of FIGS. 1A-B) may include a first arrangement of magnets in its connector, while the pressure-mitigation apparatus designed for non-elongated support surfaces (e.g., pressure-mitigation apparatus of FIGS. 2A-B) may include a second arrangement of magnets in its connector. The controller 600 may include one or more sensor(s) arranged near the fluid interface 608 for detecting whether magnets are located within a specified proximity. The controller 600 may automatically determine, based on which magnets have been detected by the sensor(s), which type of pressure-mitigation apparatus is connected. For example, pressure-mitigation devices may have different geometries, layouts, and/or dimensions suitable for various different patient positions (e.g., supine, prone, sitting), the support surface on which they are designed to reside (e.g., wheelchair, bed, recliner, surgical table), and/or patient characteristics (e.g., indication, size), and the controller can be configured to automatically detect the type of pressure-mitigation device connected thereto. In some embodiments, the automatic detection is performed using other suitable identification mechanisms, such as the controller device 600 reading an RFID tag or bar code on the pressure-mitigation device. As further described below, the controller 600 can be configured to dynamically alter the pattern for inflating chambers based on which type of pressure-mitigation apparatus is connected.

The controller 600 may also include a display 610 for displaying information related to the pressure-mitigation apparatus, the pattern of inflations/deflations, the patient, etc. For example, the display 610 may present an interface that specifies which type of pressure-mitigation apparatus (e.g., pressure-mitigation apparatus 100, 200, 300 of FIGS. 1A-3) is connected to the controller 600. Other display technologies could also be used to convey information to an operator of the controller 600. In some embodiments, the controller 600 includes a series of lights (e.g., light-emitting diodes) that are representative of different statuses to provide visual alerts to the operator or user. For example, a status light may provide a green visual indication if the controller 600 is presently providing therapy, a yellow visual indication if the controller 600 has been paused (i.e., is in a pause mode), a red visual indication if the controller 600 has experienced an issue (e.g., noncompliance of patient, patient not detected on device) or requires maintenance (i.e., is in an alert mode), etc. These visual indications may dim upon the conclusion of a specified period of time or upon determining that the status has changed (e.g., the pause mode is no longer active).

In some embodiments, the controller device 600 can also include a quick or rapid deflate function that allows a clinician to rapidly deflate all or a portion (e.g., the side chambers) of the pressure-mitigation device. This is a software solution provided by the controller device 600 and activated via the display 610 (e.g., when configured as a user interface with touchscreen buttons) and/or tactile actuators (e.g., buttons) on the device. This rapid deflation, in particular the deflation of the side pillows, is expected to be beneficial to clinicians when there is a need for quick access to the patient, such as to provide CPR.

Figure 7:
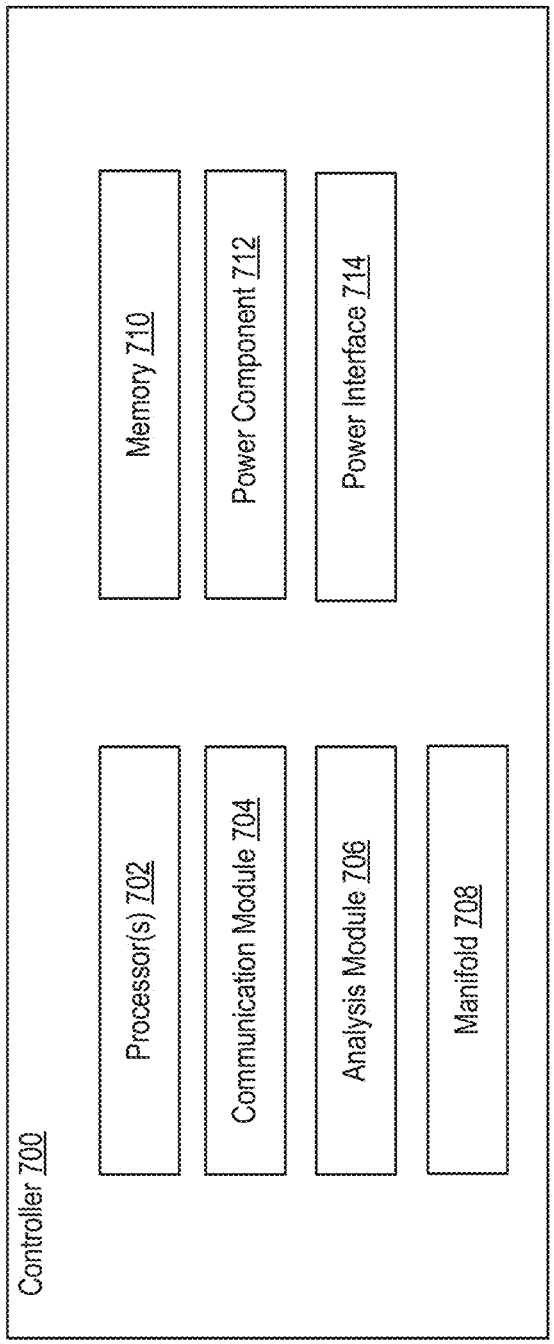
FIG. 7 is a block diagram illustrating exemplary components of a controller configured in accordance with embodiments of the present technology.

FIG. 7 is a block diagram illustrating components of a controller 700 in accordance with embodiments of the present technology. The controller 700 can include one or more processors 702, a communication module 704, an analysis module 706, a manifold 708, a memory 710, and/or a power component 712 that is electrically coupled to a power interface 714. These components may reside within a housing (also referred to as a "structural body"), such as the controller device housing 602 described above with respect to FIGS. 6A-6C. In some embodiments, the controller 700 can be incorporated in other housings or components of a pressure mitigation system, including being remotely coupled to a pressure-mitigation device. Embodiments of the controller 700 can include any subset of the components shown in FIG. 7, as well as additional components not illustrated here. For example, some embodiments of the controller 700 include a physical data interface through which data can be transmitted to another computing device. Examples of physical data interfaces include Ethernet ports, Universal Serial Bus (USB) ports, and proprietary ports.

The controller 700 may be connected to a pressure-mitigation apparatus that includes a series of chambers whose pressure can be individually varied. When the pressure-mitigation apparatus is placed between a human body and a support surface, the controller 700 can cause the pressure on an anatomical region of the human body to be varied by controllably inflating one or more chambers, deflating one or more chambers, or any combination thereof. Such action can be accomplished by the manifold 708, which controls fluid flow to the series of chambers of the pressure-mitigation apparatus. The manifold 708 is further described with respect to FIGS. 8 and 9.

As further described below, transducers mounted in the manifold 708 can generate an electrical signal based on the pressure detected in the chambers of the pressure-mitigation apparatus. Generally, each chamber is associated with a different fluid channel and a different transducer. Accordingly, if the manifold 708 is designed to facilitate fluid flow to a four-chamber pressure-mitigation apparatus, the manifold 708 may include four fluid channels and four transducers. In some embodiments, the manifold 708 may include fewer than four fluid channels and/or transducers or greater than four fluid channels and/or transducers. Pressure data representative of the values of the electrical signals generated by the transducers can be stored, at least temporarily, in the memory 710. In some embodiments, the processor(s) 702 processes the pressure data prior to examination by the analysis module 706. For example, the processor(s) 702 may apply algorithms designed for temporal aligning, artifact removal, and the like.

By examining the pressure data in conjunction with flow data representative of fluid flowing into the controller 700 from the pump(s), the analysis module 706 can control how the chambers of the pressure-mitigation apparatus are inflated and/or deflated. For example, the analysis module 706 may be responsible for separately controlling the set point for fluid flow to each chamber.

Moreover, by examining the pressure data, the analysis module 706 may be able to sense movements of the human body under which the pressure-mitigation apparatus is positioned. These movements may be caused by the patient, another individual (e.g., a caregiver or an operator of the controller 700), or the underlying support surface. The analysis module 706 may apply algorithm(s) to the data representative of these movements (also referred to as "movement data" or "motion data") to identify repetitive movements and/or random movements to better understand the health state of the patient. For example, the analysis module 706 may be able to establish respiration rate or heart rate based on the movements of a patient. Generally, the movement data can be derived from the pressure data. Consequently, the pressure-mitigation apparatus may not actually include any sensors for measuring movement, such as accelerometers, tilt sensors, or gyroscopes.

Following examination of the pressure data, the analysis module 706 may respond in several ways. For example, the analysis module 706 may generate a notification (e.g., an alert) to be transmitted to another computing device by the communication module 704. The other computing device may be associated with a healthcare professional (e.g., a physician or a nurse), a family member of the patient, or some other entity (e.g., a researcher or an insurer). The communication module 704 may communicate with the other computing device via a bi-directional communication protocol, such as Near Field Communication (NFC), wireless USB, Bluetooth, Wi-Fi, a cellular data protocol (e.g., LTE, 3G, 4G, or 5G), or a proprietary point-to-point protocol. As another example, the analysis module 706 may cause the pressure data (or analyses of such data) to be integrated with the electronic health record of the patient. Generally, the electronic health record is maintained in a storage medium accessible to the communication module 704 across a network.

The controller 700 may include a power component 712 able to provide to the other components residing within the housing, as necessary. Examples of power components include rechargeable lithium-ion (Li-Ion) batteries, rechargeable nickel-metal hydride (NiMH) batteries, rechargeable nickel-cadmium (NiCad) batteries, etc. In some embodiments, the controller 700 does not include a power component, and thus must receive power from an external source. In such embodiments, a cable designed to facilitate the transmission of power (e.g., via a physical connection of electrical contacts) may be connected between the power interface 714 of the controller 700 and the external source. The external source may be, for example, an alternating current (AC) power socket or another electronic device.

Figure 8:
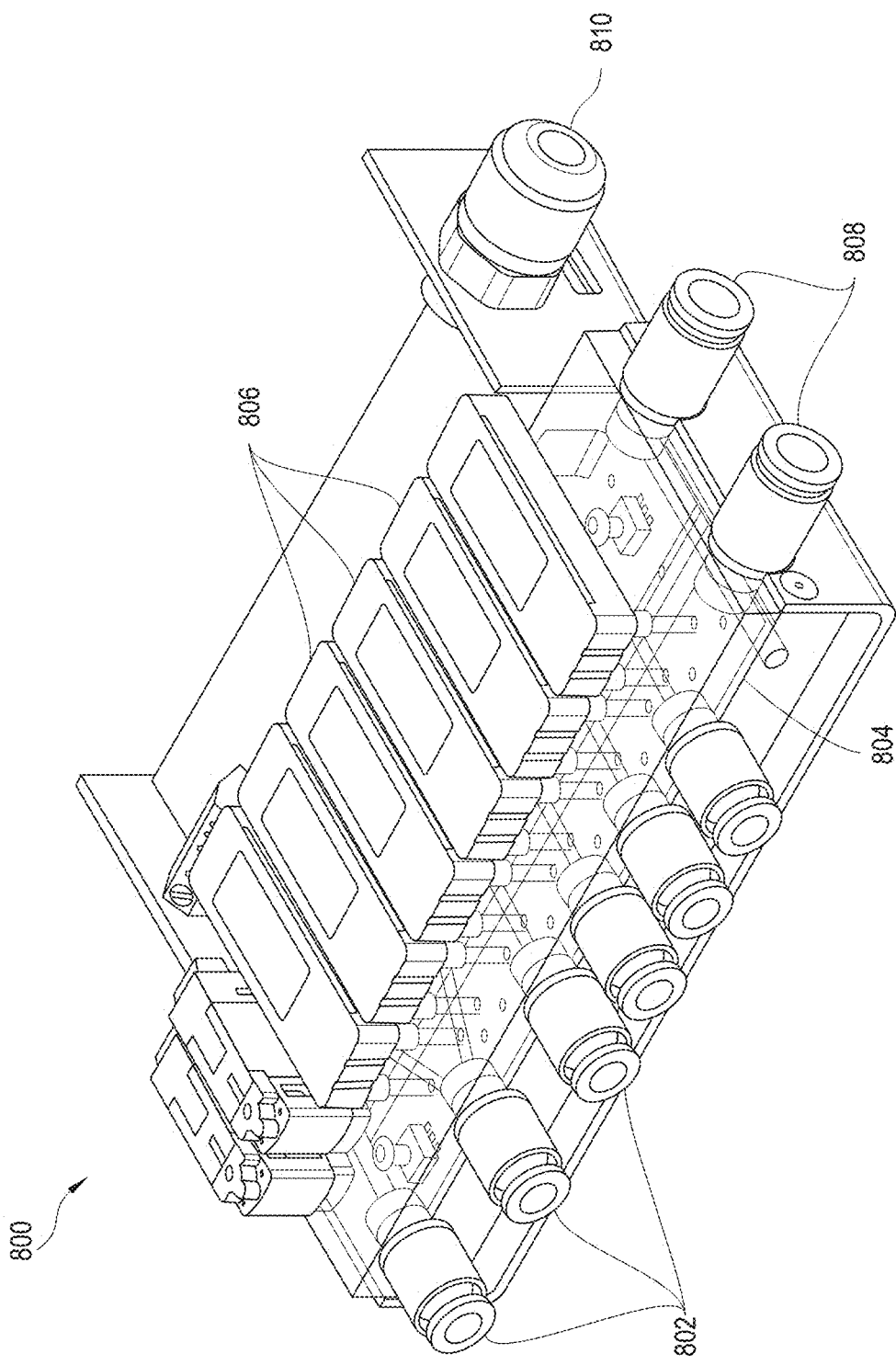
FIG. 8 is an isometric view of a manifold for controlling fluid flow to chambers of a pressure-mitigation apparatus in accordance with embodiments of the present technology.

FIG. 8 is an isometric view of a manifold 800 for controlling fluid flow (e.g., air flow) to the chambers of a pressure-mitigation apparatus in accordance with embodiments of the present technology. As described above, a controller can be configured to inflate and/or deflate the chambers of a pressure-mitigation apparatus. To accomplish this, the manifold 800 can guide fluid to the chambers through a series of valves 802. In some embodiments, each valve 802 corresponds to a separate chamber of the pressure-mitigation apparatus. In some embodiments, at least one valve 802 corresponds to multiple chambers of the pressure-mitigation apparatus. In some embodiments, at least one valve 802 is not used during operation. For example, if the pressure-mitigation apparatus includes four chambers, multi-channel tubing may be connected between the pressure-mitigation apparatus and four valves 802 of the manifold 800. In such embodiments, the other valves may remain sealed during operation.

Generally, the valves 802 are piezoelectric valves designed to switch from one state (e.g., an open state) to another state (e.g., a closed state) upon in response to an application of voltage. Piezoelectric valves provide several benefits over other valves, such as linear valves and solenoid-based valves. First, piezoelectric valves do not require holding current to maintain a state. As such, piezoelectric valves generate almost no heat. Second, piezoelectric valves create almost no noise when switching between states, which can be particularly useful in medical settings. Third, piezoelectric valves can be opened and closed in a controlled manner that allows the manifold 800 to precisely approach a given flow rate without overshoot or undershoot. In contrast, the other valves described above must be in either an open state, in which the valve is completely open, or a closed state, in which the valve is completely closed. Fourth, piezoelectric valves require very little power to operate, so a power component of the controller (e.g., power component 712 of FIG. 7) may only need to provide 3-6 watts to the manifold 800 at any given time. While embodiments of the manifold 800 may be described in the context of piezoelectric valves, other types of valves, such as linear valves or solenoid-based valves, could be used instead of, or in addition to, piezoelectric valves.

Each piezoelectric valve includes at least one piezoelectric element that acts as an electromechanical transducer. When a voltage is applied to the piezoelectric element, the piezoelectric element is deformed, thereby resulting in mechanical motion (e.g., the opening or closing of a valve). Examples of piezoelectric elements include disc transducers, bender actuators, and piezoelectric stacks.

In some embodiments, the manifold 800 includes one or more transducers 806 and a circuit board 804 that includes one or more integrated circuits (also referred to as "chips") for managing communication with the valves 802 and the transducer(s) 806. Because these local chip(s) reside within the manifold 800 itself, the valves 802 can be digitally controlled in a precise manner. The local chip(s) may also be connected to other components of the controller. For example, the local chip(s) may be connected to processor(s) (e.g., processor(s) 702 of FIG. 7) housed within the controller. The transducer(s) 806, meanwhile, can generate an electrical signal based on the pressure of each chamber of the pressure-mitigation apparatus. Generally, each chamber is associated with a different valve 802 and a different transducer 806. Here, for example, the manifold includes six valves 802 capable of interfacing with the pressure-mitigation apparatus, and each of these valves is associated with a corresponding transducer 802. Pressure data representative of the values of the electrical signals generated by the transducer(s) 806 can be provided to other components of the controller for further analysis.

The manifold 800 may also include one or more compressors. In some embodiments each valve 802 of the manifold 800 is fluidically coupled to the same compressor, while in other embodiments each valve 802 of the manifold 800 is fluidically coupled to a different compressor. Each compressor can increase the pressure of fluid (e.g., air) by reducing its volume before guiding the fluid to the pressure-mitigation apparatus.

Fluid produced by a pump may initially be received by the manifold 800 through one or more ingress fluid interfaces 808. As noted above, in some embodiments, a compressor may then increase pressure of the fluid by reducing its volume. Thereafter, the manifold 800 can controllably guide the fluid into the chambers of a pressure-mitigation apparatus through the valves 802. The flow of fluid into each chamber can be controlled by local chip(s) disposed on the circuit board 804. For example, the local chip(s) can dynamically vary the flow of fluid into each chamber in real time by controllably applying voltages to open/close the valves 802.

In some embodiments, the manifold includes one or more egress fluid interfaces 810. The egress fluid interface(s) 810 may be designed for high pressure and high flow to permit rapid deflation of the pressure-mitigation apparatus. For example, upon determining that an operator has provided input indicative of a request to deflate the pressure-mitigation apparatus (or a portion thereof), the manifold 800 may allow fluid to travel back though the valve(s) 802 from the pressure-mitigation apparatus and then out through the egress fluid interface(s) 810. Thus, the egress fluid interface(s) 810 may also be referred to as "exhausts" or "outlets." To provide the input, the operator may interact with a mechanical input component (e.g., mechanical input component 606 of FIG. 6A) or a digital input component (e.g., visible on display 610 of FIG. 6A).

Figure 9:
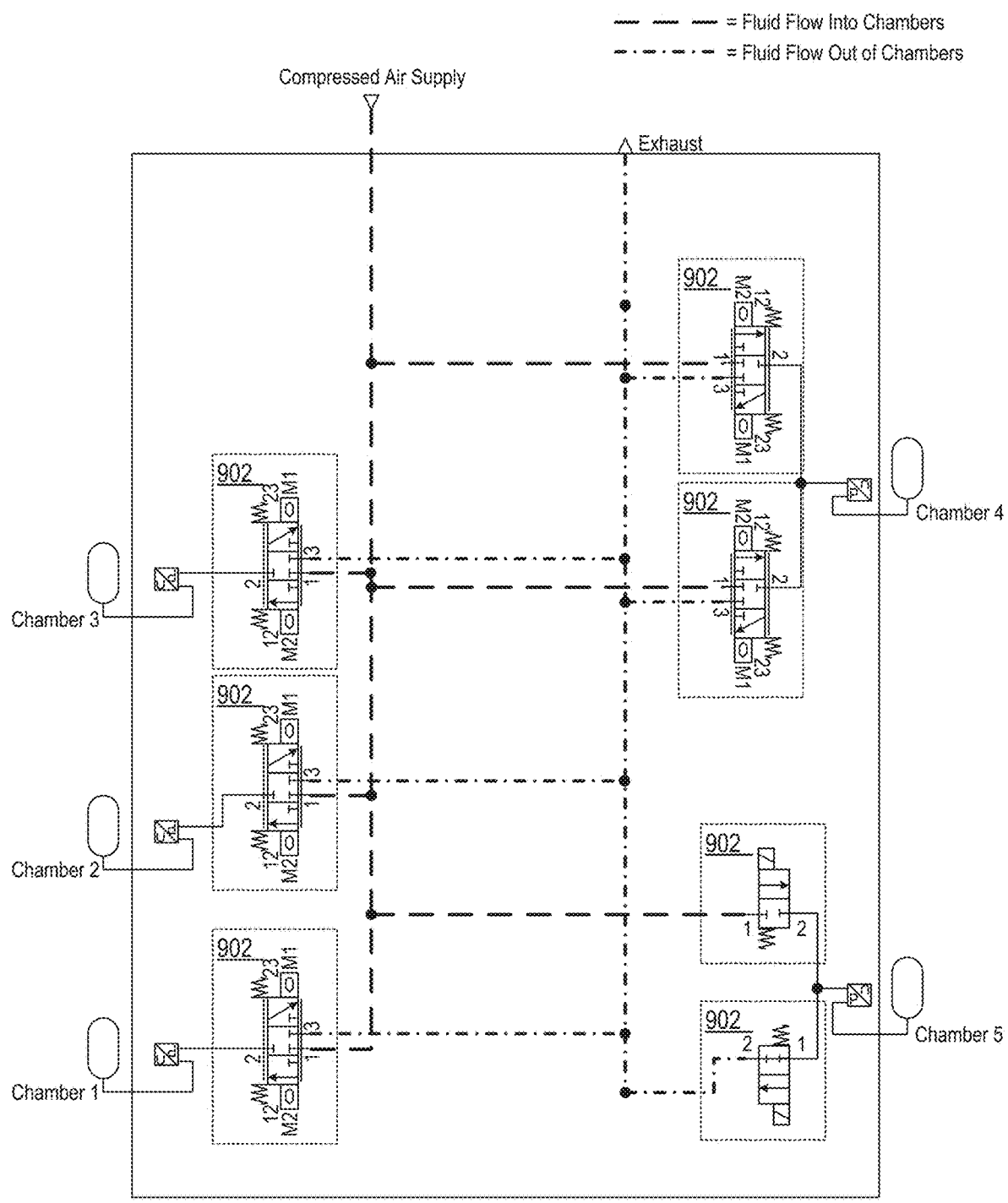
FIG. 9 is an electrical diagram illustrating piezoelectric valves of a manifold for separately controlling fluid flow along multiple channels in accordance with embodiments of the present technology.

FIG. 9 is a generalized electrical diagram illustrating how the piezoelectric valves 902 of a manifold can separately control fluid flow along multiple channels in accordance with embodiments of the present technology. In FIG. 9, the manifold includes seven piezoelectric valves 902. In other embodiments, the manifold may include less than seven valves or more than seven valves. Fluid can be guided by the manifold through the piezoelectric valves 902 to the chambers of a pressure-mitigation apparatus. In FIG. 9, the manifold 900 is fluidically connected to a pressure-mitigation apparatus that includes five chambers. However, in other embodiments, the manifold 900 may be fluidically connected to a pressure-mitigation apparatus that includes less than five chambers or more than five chambers.

All of the piezoelectric valves 902 included in the manifold need not necessarily be identical to one another. Piezoelectric valves may be designed for high pressure and low flow, high pressure and high flow, low pressure and low flow, or low pressure and high flow. In some embodiments all of the piezoelectric valves included in the manifold are the same type, while in other embodiments the manifold includes multiple types of piezoelectric valves. For example, piezoelectric valve(s) corresponding to side supports of the pressure-mitigation apparatus may be designed for high pressure and high flow (e.g., to allow for a quick discharge of fluid), but piezoelectric valve(s) corresponding to chambers of the pressure-mitigation apparatus may be designed for high pressure and low flow. Moreover, some piezoelectric valves may support bidirectional fluid flow, while other piezoelectric valves may support unidirectional fluid flow. Generally, if the manifold 900 includes unidirectional piezoelectric valves, each chamber in the pressure-mitigation apparatus is associated with a pair of unidirectional piezoelectric valves to allow fluid flow in either direction. Here, for example, Chambers 1-3 are associated with a single bidirectional piezoelectric valve, Chamber 4 is associated with two bidirectional piezoelectric valves, and Chamber 5 is associated with two unidirectional piezoelectric valves.

The manifold of the controller can be configured to inflate and/or deflate each chamber of a pressure-mitigation apparatus to achieve a specified pressure value. FIG. 10 is a table summarizing illustrating a sequence for inflating chambers in accordance with embodiments of the present technology. The table shown here corresponds to the diagram of FIG. 9. Accordingly, Chamber 1 (C1), Chamber 2 (C2), and Chamber 3 (C3) correspond to the geometric arrangement of chambers to be positioned beneath various portions of a human body (e.g., a sacral region, a back region, an abdominal region), Chamber 4 (C4) corresponds to the side support(s), and Chamber 5 (C5) corresponds to a chamber that extends under at least a portion of the legs of the human body to relieve pressure along the legs and/or feet (e.g., lift the heels of the human body positioned thereon).

Each value associated with a chamber (i.e., C1-05) corresponds to a given pressure value. For example, in step 1, the controller causes C1 to be pressurized to 30 millimeters of mercury (mmHg), C2 to be pressurized to 45 mmHg, C3 to be pressurized to 30 mmHg, and so on. Each step may require that the pressure of each chamber be held substantially constant for a specified duration (e.g., 30 seconds, 45 seconds, 60 seconds 90) before proceeding on to the next step. Each step may have an equal duration of 15 seconds, 30 seconds, 45 seconds, 60 seconds, or 120 seconds, and in other embodiments, certain steps may have differing durations. Steps may have a duration shorter than 15 seconds or longer than 120 seconds. In some embodiments, only some of these steps are performed. For example, step 0 may only be performed if the controller is connected to an elongated pressure-mitigation apparatus (e.g., pressure-mitigation apparatus 100 of FIGS. 1A-B).

As described above, the controller can be configured to detect which type of pressure-mitigation apparatus has been connected to the controller (and thus how many chambers need to be controlled). If the controller discovers that the pressure-mitigation apparatus includes less than five chambers, the controller can dynamically alter the pattern by disabling the valve(s) corresponding to whichever chamber(s) are not present. For example, if the controller determines that the pressure-mitigation apparatus does not include side supports, the controller may disable the valve(s) associated with C4.

The pressure level of a given chamber may be automatically offset by the controller based on input manually provided by an operator and/or input automatically acquired by the controller. For example, the pressure level of the individual chambers can be offset depending on the weight of the patient supported by the pressure-mitigation apparatus, the position of the patient when supported by the pressure-mitigation apparatus (e.g., seated, reclined, supine, or prone), the surface on which the pressure-mitigation apparatus is positioned (e.g., stiff or flexible), and/or other characteristics of the patient and/or the support surface that may affect the pressure imparted onto the patient. These parameters can be input into the controller (e.g., via the controller device 600 of FIGS. 6A-6C) and/or detected via the pressure-mitigation system. For example, the pressure-mitigation system can detect the patient's weight and/or position on the pressure-mitigation device by remote pressure monitoring of the chambers and/or detect the type of pressure-mitigation device operably coupled to the controller device. Table I includes several examples of offsets that may be applied by the controller. In some embodiments, these offsets may be combined depending upon the characteristics of the patient and the pressure-mitigation device, and this offset can be incorporated into the pressure mitigation inflation protocol.

TABLE I

Examples of offsets that may be automatically applied by the controller on behalf of an operator.

Offset Table

| | |
|---|---|
| Bed | +5 mmHg |
| Chair | +7 mmHg |
| 0-45 kilogram (kg) | −8 mmHg |
| 45-57 kg | −6 mmHg |
| 57-68 kg | −4 mmHg |
| 68-80 kg | −2 mmHg |
| 80-91 kg | 0 mmHg |
| 91-102 kg | +2 mmHg |
| 102-113 kg | +4 mmHg |
| 113-125 kg | +6 mmHg |
| 125-136 kg | +8 mmHg |
| 136-181 kg | +10 mmHg |

Chambers may be inflated/deflated for a predetermined duration of 15-180 seconds (e.g., 30 seconds, 60 seconds, 90 seconds, 120 seconds, 150 seconds, or any duration therebetween) and to a predetermined pressure level from 0-100 mmHg (e.g., 15 mmHg, 20 mmHg, 30 mmHg, 45 mmHg, 50 mmHg, or any pressure level therebetween). In other embodiments, the duration of inflation may be longer or shorter and/or the pressure levels may be lower or higher. In some embodiments, the inflation pattern administered by the controller inflates/deflates two or more chambers at one time. In these embodiments, the chambers can be inflated/ deflated to the same or different pressure levels, and the duration that the chambers are maintained at the pressure levels may be the same or different. In other embodiments, the controller can apply different inflation/deflation patterns to the individual chambers.

FIG. 11 is a flow diagram of a process 1100 for varying pressure in chambers of a pressure-mitigation apparatus positioned between a human body and a support surface in accordance with embodiments of the present technology. By varying the pressure in the chambers, a controller can move the main point of pressure applied by the support surface across the human body. For example, the main point of pressure applied by the support surface to the human body may be moved amongst a plurality of predetermined locations by sequentially varying the pressure in different predetermined subsets of inflatable chambers.

Initially, a controller can determine that a pressure-mitigation apparatus has been connected to the controller (step 1101). By monitoring the connection between a fluid interface (e.g., fluid interface 608 of FIG. 6B) and the pressure-mitigation apparatus, the controller can detect which type of pressure-mitigation apparatus has been connected. In some embodiments, each type of pressure-mitigation apparatus may include a different type of connector. For example, the pressure-mitigation apparatus designed for elongated support surfaces (e.g., pressure-mitigation apparatus 100 of FIGS. 1A-B) may include a first arrangement of magnets in its connector, while the pressure-mitigation apparatus designed for non-elongated support surfaces (e.g., pressure-mitigation apparatus of FIGS. 2A-B) may include a second arrangement of magnets in its connector. The controller may determine which type of pressure-mitigation apparatus has been connected based on which magnets have been detected within a specified proximity. As another example, the pressure-mitigation apparatus designed for elongated support surfaces may include a beacon capable of emitting a first electronic signature, while the pressure-mitigation apparatus designed for non-elongated support surfaces may include a beacon capable of emitting a second electronic signature. Examples of beacons include Bluetooth beacons, USB beacons, and infrared beacons. A beacon may be configured to communicate with the controller via a wired communication channel or a wireless communication channel.

The controller can then identify a pattern corresponding to the pressure-mitigation apparatus (step 1102). For example, the controller may examine a library of patterns corresponding to different pressure-mitigation apparatuses to identify the appropriate pattern. The library of patterns may be stored in a local memory (e.g., memory 710 of FIG. 7) or a remote memory accessible to the controller across a network. As another example, the controller may modify an existing pattern based on the pressure-mitigation apparatus. For instance, the controller may alter the existing pattern responsive to determining that the pattern includes instructions for more chambers than the pressure-mitigation apparatus includes. The controller can then cause the chambers of the pressure-mitigation apparatus to be inflated in accordance with the pattern (step 1103). More specifically, the controller can cause the pressure on one or more anatomical regions of the human body to be varied by controllably inflating one or more chambers, deflating one or more chambers, or any combination thereof.

The controller may receive input indicative of a request to initiate a deflation procedure (step 1104). In some embodiments, the input is associated with an instruction that is manually provided by an operator (e.g., as a result of an interaction with a mechanical input component or a digital input component). For example, the operator may request that the deflation procedure be initiated before the patient is transferred to/from the pressure-mitigation apparatus. As another example, the operator may request that the deflation procedure be initiated before a medical procedure (e.g., cardiopulmonary resuscitation or defibrillation) involving the patient is performed. In other embodiments, the input is associated with an instruction that is automatically generated by the controller. The controller may automatically generate the instruction in response to a specified criterion being satisfied. For example, the controller may automatically generate the instruction when the pressure in a chamber or a side support of the pressure-mitigation apparatus exceeds an upper threshold.

Thereafter, the controller can cause deflation of a chamber, a side support, or any combination thereof (step 1105). More specifically, the controller may instruct a manifold (e.g., manifold 800 of FIG. 8) to stop supplying fluid to at least a portion of the pressure-mitigation apparatus and/or open the valve(s) corresponding to the portion of the pressure-mitigation apparatus to allow fluid to escape the pressure-mitigation apparatus.

FIG. 12 is a flow diagram of a process 1200 for establishing characteristics of the human body supported by a pressure-mitigation apparatus without placing any sensors in direct contact with the human body in accordance with embodiments of the present technology. Steps 1201-1203 of FIG. 12 may be at least generally similar to steps 1101-1103 of FIG. 11.

As described above, the controller responsible for managing inflation/deflation of the pressure-mitigation apparatus may include transducer(s) configured to generate an electrical signal based on the pressure of each chamber of the pressure-mitigation apparatus. Accordingly, the controller may acquire pressure data representative of the values of the electrical signals generated by the transducer(s) (step 1204). The controller can then examine the pressure data to identify movement(s) of the human body (step 1205). In some embodiments, the controller can transmit some or all of the pressure data to a remote location (e.g., a central server) for processing or analytics. By constantly monitoring pressures of the chambers of the pressure-mitigation apparatus, the controller can interpret information regarding the movement/location of the human body without requiring the use of sensors in direct contact with the human body.

The monitoring of patient movement via the remote pressure monitoring can be used as an indicator of the patient's mobility status and/or the overall health status of the patient, as well as identify periods of complete immobility, which may indicate a associated with patient movement can also indicate a decline in patient health status or a potential health complication. Remote pressure monitoring can also detect when a patient leaves the bed, chair, or other surface on which the patient-mitigation devices is disposed, and in some embodiments, respond to this movement with an alert or alarm provided locally or to a remote location (e.g., to a caregiver) to draw attention to this movement. This allows patient caregivers to assist when the patient is ambulatory to avoid falls and/or identify falls from the support surface in real time. The remote pressure monitoring data can also be used to determine whether the patient is properly using the device, whether he or she is properly positioned on the pressure-mitigation surface, whether the patient is complying with the prescribed protocol. Based on this information, alerts or alarms transmitted to a remote system accessible by a hospital, caregiver, and/or other individuals involved with the patient's care. The real-time monitoring and analysis of data can provide accurate alarms to alert caregivers, management, and others when the patient is not compliant with the protocol and/or improperly using the device (e.g., positioned incorrectly), thereby promoting appropriate usage and enhancing the benefit of the pressure mitigation system.

The controller (or some other electronic device, such as a mobile phone, laptop computer, or computer server) can estimate a characteristic of the human body based on the pressure data, the movement(s), or any combination thereof (step 1206). For example, the controller may be able to estimate the weight of the human body by examining the pressure data in conjunction with flow data representative of fluid flowing into the controller (e.g., from one or more pumps). As another example, the controller may be able to estimate the respiration rate or heart rate of the human body based on the movements. Accordingly, the controller may be able to understand certain aspects of the health state of the human body, such as mobility state, in a noninvasive manner.

Unless contrary to physical possibility, it is envisioned that the steps described above may be performed in various sequences and combinations. For example, the controller may be configured to perform the process 1100 of FIG. 11 and the process 1200 of FIG. 12 simultaneously. Other steps may also be included in some embodiments. For example, the controller may cause a notification to be transmitted to another computing device in certain situations (e.g., upon discovering movement indicative of discomfort in a specified anatomical region of the human body, movement indicative of an attempt to leave the pressure-mitigation apparatus, or a complete lack of movement for a specified period of time).

Selected Embodiments of Pressure-Mitigation Systems

Figure 13:
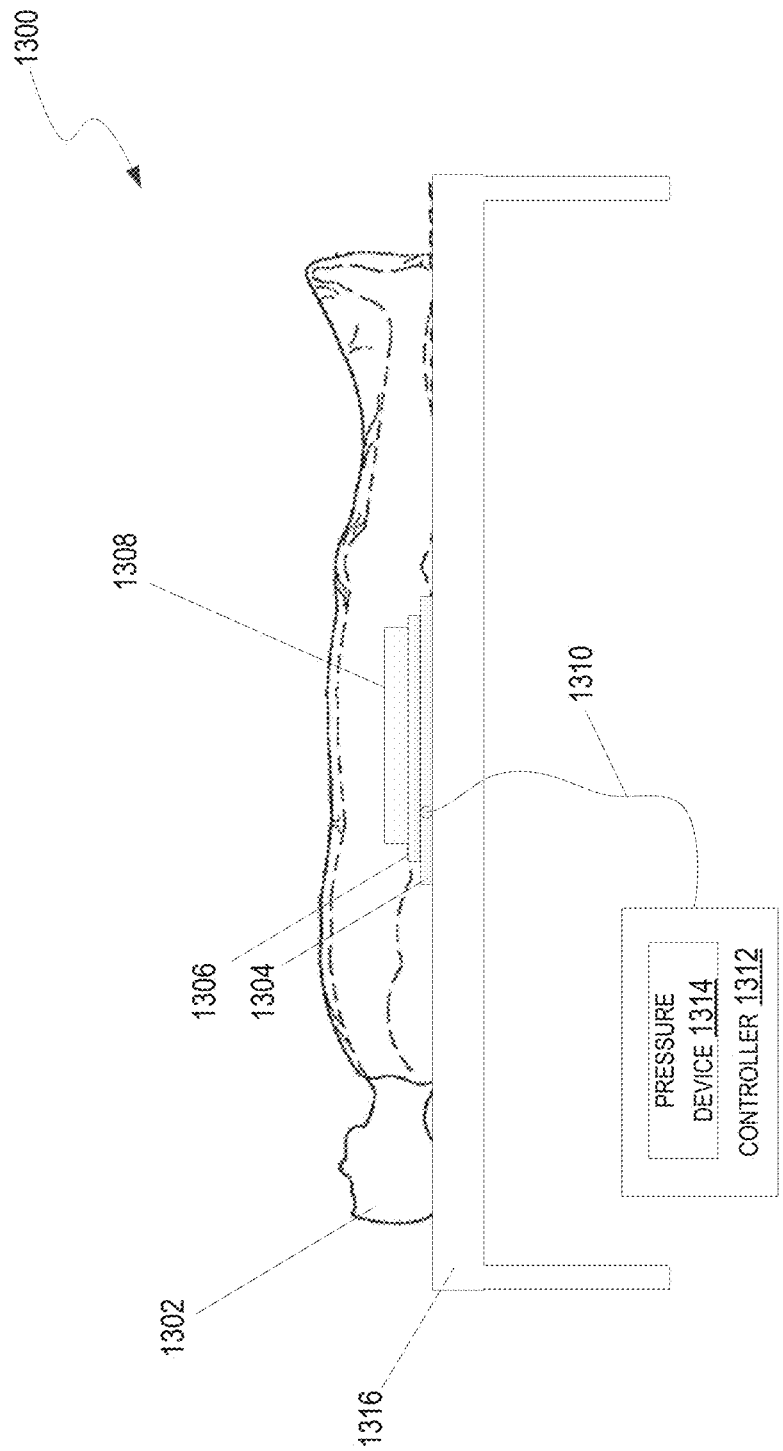
FIG. 13 is a partially schematic side view of a pressure-mitigation system for orienting an individual over a pressure-mitigation apparatus in accordance with embodiments of the present technology.

FIG. 13 is a partially schematic side view of a pressure-mitigation system 1300 (or simply "system") for orienting an individual 1302 over a pressure-mitigation apparatus 1306 in accordance with embodiments of the present technology. The system 1300 can include a pressure-mitigation apparatus 1306 that include side supports 1308, an attachment apparatus 1304, a pressure device 1314, and a controller 1312. As shown in FIG. 10, the attachment apparatus 1304 may be responsible for securing the pressure-mitigation apparatus 1306 to the support surface 1316. Further examples of the attachment apparatus are discussed in detail with respect to FIGS. 1-3, and further examples of the pressure-mitigation apparatus are discussed in detail with respect to FIGS. 4A-6.

In this embodiment, the pressure-mitigation apparatus 1306 includes a pair of optional elevated side supports 1308 that extend longitudinally along opposing sides of the pressure-mitigation apparatus 1306. The pressure-mitigation apparatus 1306 includes a series of chambers interconnected on a base material. As further described above, the chambers may be arranged in a geometric pattern designed to mitigate the pressure applied to a specific anatomical region by the support surface 1316.

The elevated side supports 1308 can be configured to actively orient the specific anatomical region of the individual 1302 over the series of chambers. For example, the elevated side supports 1308 may be responsible for actively orienting the specific anatomical region widthwise over the epicenter of the geometric pattern. As shown in FIG. 10, the specific anatomical region may be the sacral region. However, the specific anatomical region could be any region of the body that is susceptible to pressure, and thus the formation of pressure ulcers. The elevated side supports 1308 may be configured to be ergonomically comfortable. For example, the elevated side supports 1308 may include a recess designed to accommodate the forearm, which permits pressure to be offloaded from the elbow.

The elevated side supports 1308 may be significantly larger in size as compared to the chambers of the pressure-mitigation apparatus 1306. Accordingly, the elevated side supports 1308 may create a barrier that restricts lateral movement of the individual 1302. In some embodiments, the elevated side supports are approximately 2-3 inches taller in height as compared to the average height of an inflated chamber. Because the elevated side supports 1306 straddle the individual 1302, the elevated side supports 1308 can act as barriers for maintaining the position of the individual 1302 on top of the pressure-mitigation apparatus 1306. In some embodiments, the elevated side supports 1308 may be omitted.

In some embodiments, the inner side walls of the elevated side supports 1308 form, following inflation, a firm surface at a steep angle of orientation with respect to the pressure-mitigation apparatus 1306. For example, the inner side walls may be on a plane of approximately 115 degrees, plus or minus 24 degrees, from the plane of the pressure-mitigation apparatus 1306. These steep inner side walls can form a channel that naturally positions the individual 1302 over the chambers of the pressure-mitigation apparatus 1306. Thus, inflation of the elevated side supports 1308 may actively force the individual 1302 into the appropriate position for mitigating pressure by orienting the individual 1302 in the correct location with respect to the chambers of the pressure-mitigation apparatus 1306.

After the initial inflation cycle has been completed, the pressure of each elevated side support 1308 may be lessened to increase comfort and prevent excessive force against the lateral sides of the individual 1302. Oftentimes a medical professional (e.g., a physician, nurse, or caregiver) will be present during the initial inflation cycle to ensure the elevated side supports 1308 properly position the individual 1302 over the pressure-mitigation apparatus 1306.

The controller 1312 can be configured to regulate the pressure of each chamber included in the pressure-mitigation apparatus 1306 and/or each elevated side support 1308 via a pressure device 1314 (e.g., an air pump) and multi-channel tubing 1310. For example, the chambers may be controlled in a specific pattern to preserve blood flow and reduce pressure applied to the individual 1302 when inflated (pressurized) and deflated (depressurized) in a coordinated fashion by the controller 1312. The multi-channel tubing 1310 may be connected between the pressure-mitigation apparatus 1306 and the pressure device 1314. Accordingly, the pressure-mitigation apparatus 1306 may be fluidically coupled to a first end of the multi-channel tubing 1310, and the pressure device 1314 may be fluidically coupled to a second end of the multi-channel tubing 1310.

Processing System

Figure 14:
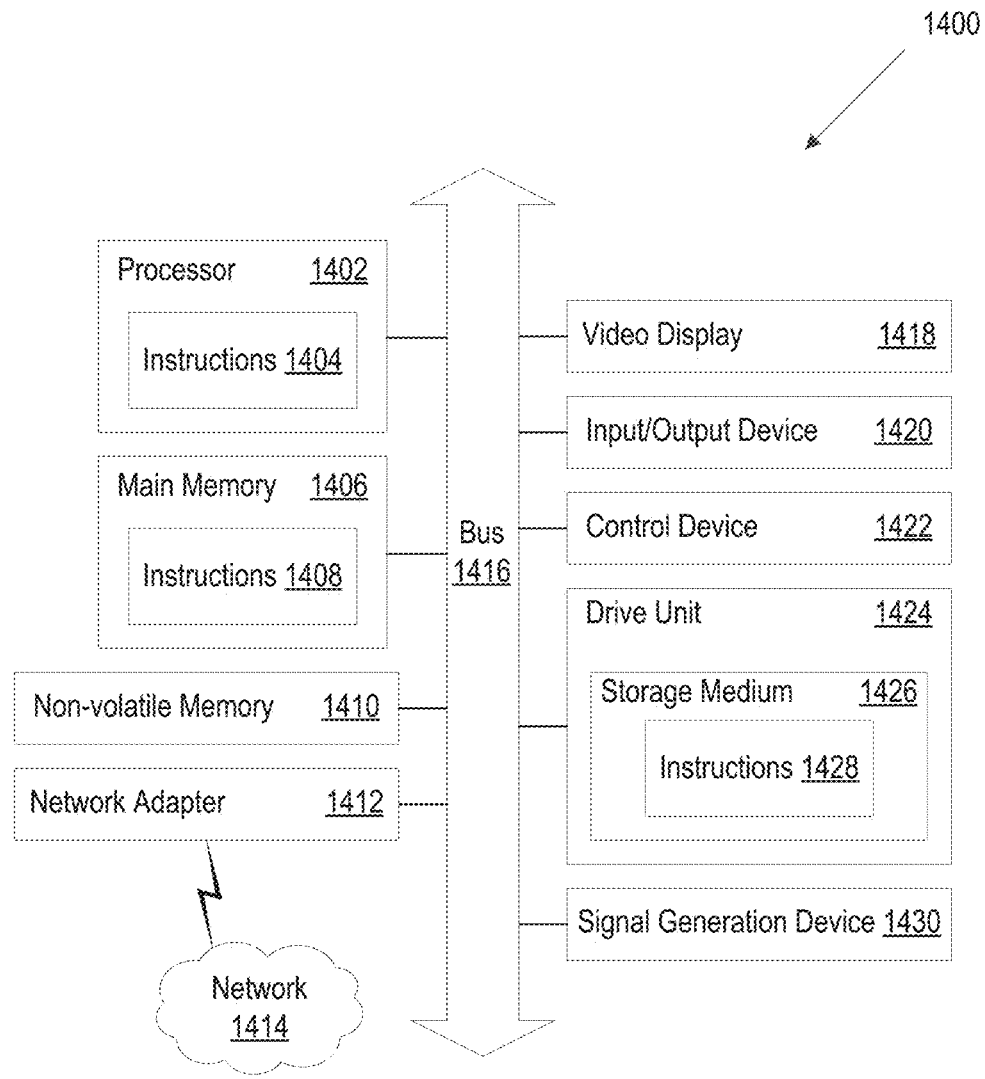
FIG. 14 is a block diagram illustrating a processing system in which at least some operations described herein can be implemented.

FIG. 14 is a block diagram illustrating a processing system 1400 in which at least some operations described herein can be implemented. For example, some components of the processing system 1400 may be hosted on a controller (e.g., controller 1312 of FIG. 13) responsible for controlling a pressure-mitigation apparatus (e.g., pressure-mitigation apparatus 1306 of FIG. 13).

The processing system 1400 may include one or more central processing units ("processors") 1402, main memory 1406, non-volatile memory 1410, network adapter 1412 (e.g., network interface), video display 1418, input/output devices 1420, control device 1422 (e.g., keyboard and pointing devices), drive unit 1424 including a storage medium 1426, and signal generation device 1430 that are communicatively connected to a bus 1416. The bus 1416 is illustrated as an abstraction that represents one or more physical buses and/or point-to-point connections that are connected by appropriate bridges, adapters, or controllers. The bus 1416, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus (also referred to as "Firewire").

The processing system 1400 may share a similar computer processor architecture as that of a desktop computer, tablet computer, personal digital assistant (PDA), mobile phone, game console, music player, wearable electronic device (e.g., a watch or fitness tracker), network-connected ("smart") device (e.g., a television or home assistant device), virtual/augmented reality systems (e.g., a head-mounted display), or another electronic device capable of executing a set of instructions (sequential or otherwise) that specify action(s) to be taken by the processing system 1400.

While the main memory 1406, non-volatile memory 1410, and storage medium 1426 (also called a "machine-readable medium") are shown to be a single medium, the term "machine-readable medium" and "storage medium" should be taken to include a single medium or multiple media (e.g., a centralized/distributed database and/or associated caches and servers) that store one or more sets of instructions 1428. The term "machine-readable medium" and "storage medium" shall also be taken to include any medium that is capable of storing, encoding, or carrying a set of instructions for execution by the processing system 1400.

In general, the routines executed to implement the embodiments of the disclosure may be implemented as part of an operating system or a specific application, component, program, object, module, or sequence of instructions (collectively referred to as "computer programs"). The computer programs typically comprise one or more instructions (e.g., instructions 1404, 1408, 1428) set at various times in various memory and storage devices in a computing device. When read and executed by the one or more processors 1402, the instruction(s) cause the processing system 1400 to perform operations to execute elements involving the various aspects of the disclosure.

Moreover, while embodiments have been described in the context of fully functioning computing devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices 1410, floppy and other removable disks, hard disk drives, optical disks (e.g., Compact Disk Read-Only Memory (CD-ROMS), Digital Versatile Disks (DVDs)), and transmission-type media such as digital and analog communication links.

The network adapter 1412 enables the processing system 1400 to mediate data in a network 1414 with an entity that is external to the processing system 1400 through any communication protocol supported by the processing system 1400 and the external entity. The network adapter 1412 can include a network adaptor card, a wireless network interface card, a router, an access point, a wireless router, a switch, a multilayer switch, a protocol converter, a gateway, a bridge, bridge router, a hub, a digital media receiver, and/or a repeater.

The network adapter 1412 may include a firewall that governs and/or manages permission to access/proxy data in a computer network, and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall may additionally manage and/or have access to an access control list that details permissions including the access and operation rights of an object by an individual, a machine, and/or an application, and the circumstances under which the permission rights stand.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We Claim:

1. A method for controlling a pressure-mitigation apparatus that is disposed between a human body and a surface, the method comprising:
   determining, by a controller, that the pressure-mitigation apparatus is fluidically coupled to an egress interface of the controller based on an analysis of an output produced by a sensor that is proximate to the egress interface;
   identifying, by the controller from among a plurality of programmable patterns, a programmable pattern that is associated with the pressure-mitigation apparatus to which the controller is fluidically coupled; and
   inflating, by the controller, each chamber of a plurality of chambers of the pressure-mitigation apparatus to varying degrees in accordance with the programmable pattern through controlled operation of a plurality of valves, each of which regulates fluid flow into a different one of the plurality of chambers, thereby shifting a point of contact pressure applied by the surface to the human body over time.

2. The method of claim 1 wherein said determining is based on a number of magnets that are detected by the sensor and located within a specified proximity of the egress interface.

3. The method of claim 2 further comprising:
   identifying, by the controller, a type of pressure-mitigation apparatus fluidically coupled to the egress interface based on the number of magnets that are located within the specified proximity.

4. The method of claim 3 wherein the programmable pattern corresponds to the type of pressure-mitigation apparatus.

5. The method of claim 1 further comprising:
   receiving, by the controller, input indicative of a request to initiate a deflation procedure; and
   causing, by the controller, deflation of at least one chamber of the pressure-mitigation apparatus.

6. The method of claim 5 wherein the request is manually provided by an operator through an interaction with a mechanical input component of the controller.

7. The method of claim 5 wherein the request is automatically provided by the controller responsive to a determination that the pressure of a chamber of the pressure-mitigation apparatus exceeds an upper threshold.

8. The method of claim 1 further comprising:
   acquiring, by the controller, data indicative of the pressure of each chamber of the plurality of chambers of the pressure-mitigation apparatus; and
   examining, by the controller, the data to identify movements, if any, performed by the human body.

9. The method of claim 8 further comprising:
   determining, by the controller, that the human body has performed no movements for a specified period of time; and
   causing, by the controller, a notification to be transmitted to an electronic device, wherein the notification specifies that no movements have been performed by the human body for the specified period of time.

10. The method of claim 8 further comprising:
    determining, by the controller, that the movements performed by the human body match a specified pattern; and
    causing, by the controller, a notification to be transmitted to an electronic device,
       wherein the notification specifies that the movements performed by the human body match the specified pattern.

11. The method of claim 1 further comprising:
    acquiring, by the controller, data indicative of the pressure of each chamber of the plurality of chambers of the pressure-mitigation apparatus; and
    estimating, by the controller, a characteristic of the human body based on the data.

12. The method of claim 11 wherein the characteristic is a weight, a heart rate, or a respiration rate.

13. A method performed by a first processor that resides within a controller that is fluidically coupled to a pressure-mitigation apparatus, the method comprising:
    obtaining, by the first processor, data that is representative of a first plurality of signals generated by a plurality of transducers,
       wherein each transducer is configured to generate a signal based on a pressure of a corresponding chamber of a plurality of chambers of the pressure-mitigation apparatus to which the controller is fluidically coupled;
    generating, by the first processor based on the first plurality of signals, a second plurality of signals for controlling a plurality of piezoelectric valves through which air can be delivered to the plurality of chambers of the pressure-mitigation apparatus,
       wherein each piezoelectric valve is associated with a discrete flow of air destined for a corresponding chamber of the plurality of chambers of the pressure-mitigation apparatus;
    transmitting, by the first processor, the second plurality of signals to the plurality of piezoelectric valves, so as to cause the plurality of chambers of the pressure-mitigation apparatus to be inflated to varying degrees; and
    forwarding, by the first processor, at least some of the data to a second processor that resides within the controller for further examination.

14. The method of claim 13, wherein the pressure-mitigation apparatus is disposed between a human body and a surface.

15. The method of claim 14, further comprising:
    estimating, by the controller, a characteristic of the human body based on an analysis of the first plurality of signals.

16. The method of claim 13, wherein said obtaining, said generating, and said transmitting are performed in real time such that inflation of the plurality of chambers of the pressure-mitigation apparatus is varied responsive to changes in the pressure.

17. The method of claim 1 wherein the plurality of programmable patterns correspond to different types of pressure-mitigation apparatuses having different arrangements of chambers, different sizes of chambers, or any combination thereof.

18. The method of claim 1 wherein the programmable pattern indicates how to pressurize a predetermined number of chambers, and wherein the method further comprises:

discovering, by the controller, that the pressure-mitigation apparatus to which the controller is fluidically coupled has fewer than the predetermined number of chambers; and altering, by the controller in response to said discovering, the programmable pattern to account for at least one chamber not being present.

19. A method performed by a controller that includes (i) an egress interface with a plurality of channels through which fluid is able to flow and (ii) a plurality of valves that are operable to control flow of the fluid through the plurality of channels, the method comprising:

determining that a pressure-mitigation apparatus is fluidically coupled to the egress interface based on an analysis of an output produced by a sensor that is proximate to the egress interface;

identifying, from among a plurality of programmable patterns, a programmable pattern that is associated with the pressure-mitigation apparatus; and inflating each chamber of a plurality of chambers of the pressure-mitigation apparatus to varying degrees in accordance with the programmable pattern through controlled operation of the plurality of valves, each of which regulated fluid flow into a different one of the plurality of chambers, wherein said inflating causes pressure applied by an underlying surface to be shifted across a surface of a human body that is situated on the pressure-mitigation apparatus.

* * * * *